(12) United States Patent
Giovannini et al.

(10) Patent No.: US 11,376,258 B2
(45) Date of Patent: Jul. 5, 2022

(54) PURINE DERIVATIVES AND THE USE THEREOF AS MEDICAMENT

(71) Applicant: Boehringer Ingelheim International GmbH, Ingelheim am Rhein (DE)

(72) Inventors: Riccardo Giovannini, Biberach an der Riss (DE); Dieter Wiedenmayer, Biberach an der Riss (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 16/891,566

(22) Filed: Jun. 3, 2020

(65) Prior Publication Data

US 2021/0369723 A1 Dec. 2, 2021

(30) Foreign Application Priority Data

Jun. 4, 2019 (EP) ..................................... 19178044

(51) Int. Cl.
*C07D 473/00* (2006.01)
*A61K 31/5377* (2006.01)

(52) U.S. Cl.
CPC ........ *A61K 31/5377* (2013.01); *C07D 473/00* (2013.01)

(58) Field of Classification Search
CPC ........................... C07D 473/00; A61K 31/5377
USPC ........................................ 544/264; 514/234.2
See application file for complete search history.

(56) References Cited

U.S. PATENT DOCUMENTS

2002/0055519 A1 5/2002 Thompson et al.

FOREIGN PATENT DOCUMENTS

| WO | 2003010159 A1 | 2/2003 |
| WO | 2004048364 A1 | 6/2004 |
| WO | 2006113471 A2 | 10/2006 |
| WO | 2010088408 A2 | 8/2010 |
| WO | 2014060398 A1 | 4/2014 |
| WO | 2015130905 A1 | 9/2015 |
| WO | 2016029146 | 2/2016 |
| WO | 2016029146 A1 | 2/2016 |
| WO | 2016049165 A1 | 3/2016 |
| WO | 2016100349 A2 | 6/2016 |
| WO | 2019110703 A1 | 6/2019 |

OTHER PUBLICATIONS

Mony, Allosteric Modulators of NR2B-containing NMDA receptors, Bristish Journal of Pharmacology, vol. 15y, 2009.
Niu, Synthesis of C8-alkyl-substituted purine analogues by direct alylation of 8-H purines with tetrahydrofuran, Chinese chem. letters, 2017.
Weed, Negative Allosteric Modualtors Selectiv for the NR2B subtype of the NMDA receptor, Neuropsychopharmacology, 2016.
International Search report and written optinion for PCT/EP2020/065252 dated Sep. 22, 2020.
International Search Report and Written Opinion for PCT 2018/083728 dated Feb. 4, 2019.
Murrough, "Antidepressant Efficacy of Ketamine in Treatment-Resistant Major Depression: A Two Site Randomized Controlled Trial", Am. J. Psychiatry, 2013, vol. 170, p. 1134-1142.
Singh, "Intravenous Eskatamine In Adult Treatment-Resistant Depression: A double-Blind, Double-Randomization, Placebo Controlled Study", Society of Biological Psychiatry, vol. 80, 2016, p. 424-431.
Berman, "Antidepressant effects of Ketamine in depressed patients", Biological Psychiatry, vol. 47, 2000, p. 351-354.
Krystal, "Subanesthetic Effects of the Noncompetitive NMDA Antagonist, Ketamine in Humans", Arch. Gen. Psychiatry, 1994, vol. 51, p. 199-214.
Paoletti, NMDA receptor subunit diversity: impact on receptor properties, synaptic plasticity and disease, Nature Reviews, vol. 14, 2013.
Miller, "GluN2B-contaning NMDA receptors regulate depression-like behavior and are critical for the rapid antidepressant actions of ketamine", eLife3e03581, 2014.
Kiselycznyk, "NMDA receptor subunits and associated signaling molecules mediating anti-depressant related effects of NMDA-GluN2B antagonism", Bhav. Nrain Res. 2015, p. 89-95. Jimemez-Sanchez, "The Role of GluN2A and GluN2B Subunits on the effects of NMDA receptor Antagonists in modeling Schizophrenia and treating Refractory Depression", Neuropsychopharmacology, 2014.

(Continued)

*Primary Examiner* — Jeffrey H Murray
(74) *Attorney, Agent, or Firm* — Shelley A. Jones

(57) ABSTRACT

The present invention relates to novel purines of general formula A

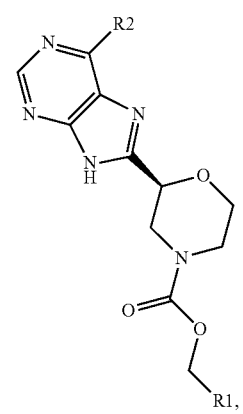

processes for their preparation, pharmaceutical compositions containing them and their use in therapy, particularly in the treatment or prevention of conditions having an association with NR2B negative allosteric modulating properties.

12 Claims, No Drawings

(56) References Cited

OTHER PUBLICATIONS

Taylor, "Absolute Oral Bioavailability of Traxoprodil in Cytochrome P450 2D6 Extensive and Poor Metabolisers", Clin. Pharmacokinet, 2006, vol. 45, p. 989-1001.
Addy, "Single dose Administration of MK-0657, an NR2B-Selective NMDA Antagonist", J. of Clinical Pharmacology, 2009, p. 856-864.
Layton, "Discovery of 3-Substituted Aminocyclopentanes as Potent and Orally Bioavailable NR2B Subtype-Selective NMDA Antagonists", ACS Chem. Neuroscience, 2011.
Traynelis, Glutamate Receptor Ion Channels: Structure, Regualtion and Function, Pharmacology reviews, 2010, vol. 62.
Chaffey, NMDA receptor subtypes, Current Anesthesia and Critical Care, 2008, vol. 19, p. 183-201.
Mony, Allosteric modulators of NR-2B-containing NMDA receptors, Bristish Journal of Pharmacology, vol. 157, 2009.
Preskom, An Innovative Design to Establish Proof of Concept of the Antidepressant effects of the NR2B Subunit Selective N-Methyl D-Aspartate Antagonist CP-101, 606, Journal of Clinical Pharmacology, vol. 28, 2008.
Beinat, Insights into Structure related activity relationships, Current Medicinal Chem, 2010. vol. 17, p. 4166-4190.
Serafini, The Role of Ketamine in Treatment resistant Depression, Current Neurapharmacology, 2014, vol. 10, p. 444-461.
Sanchez, The role of GluN2A and GluN2B Sununits on the Effects of NMDA Receptor Antagonists in Modeling Schizopgrenia and Treating Refractory Depression, Neuropsychopharmacology, vol. 30, 2014.

PURINE DERIVATIVES AND THE USE THEREOF AS MEDICAMENT

The present invention relates to novel purines of general formula A

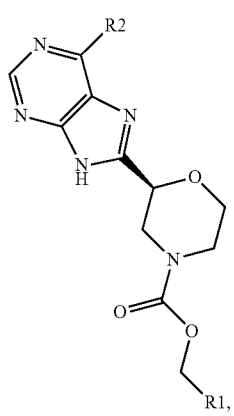

processes for their preparation, pharmaceutical compositions containing them and their use in therapy, particularly in the treatment or prevention of conditions having an association with NR2B negative allosteric modulating properties.

The compounds of the invention according to general formula A show NR2B negative allosteric modulating properties.

Extensive studies over the past twenty years have indicated that N-methyl-D-aspartate receptors (NMDA) play a relevant role in Alzheimer's disease, Parkinson's disease, dyskinesia, stroke, motor neuron disease, psychosis, epilepsy, anxiety, schizophrenia and pain.

The non-selective NMDA receptor antagonist ketamine, (racemic as well as the S enantiomer), a medication mainly used for starting and maintaining anaesthesia, has demonstrated over the last years clinical efficacy in treating major depressive disorder (MDD) at subanaesthetic doses (Murrough et al. 2013, Am J Psychiatry. 170: 1134; Singh et al. 2016, Biol Psychiatry. 80: 424). More precisely, ketamine elicits a rapid onset of efficacy which lasts several days in MDD patients insufficiently responding to standard drug therapy (Berman et al. 2000. Biol Psychiatry 47:351, Serafini et al. 2014. Curr. Neuropharmacol. 12:444). However, non-selective NMDA receptor antagonists have a range of undesirable effects which limit their application. In particular dissociative and psychogenic side effects are prominent for the non-selective NMDA receptor antagonists such as ketamine (Krystal et al. 1994. Arch. Gen. Psychiatry 51:199). In the early 1990s, it was found that multiple NMDA receptor subtypes exist, which contain different NR2(A-D) subunits (Paoletti et al., 2013 Nat Rev. Neurosci 14:383). More recently, NR2B subtype selective NMDA receptor negative allosteric modulators (NR2B NAM) have raised interest and have shown potential in a wide range of clinical indications, such as attention, emotion, mood, and pain, as well as being involved in a number of different human disorders (Mony et. al. 2009. Br. J. Pharmacol. 157:1301; Chaffey et al., Current Anaesthesia & Critical Care 19, 183). In particular, NR2B NAM have also demonstrated antidepressant efficacy in the early stage of clinical trials (Preskorn et al. 2008. J Clin Psychopharmacol 70:58).

Preclinical studies using NR2B NAM as well as applying various transgenic mice strains have shown that NR2B containing NMDA-receptors are mediating the positive effect of ketamine in e.g. the Forced Swim Test (Miller et al. 2014 eLife 3:e03581; Kiselycznyk et al. 2015, Behav Brain Res, 287:89). Furthermore, selective NR2B NAM have advantages over unselective NMDA receptor antagonists, such as ketamine, due to greatly diminished dissociative and psychotomimetic side effects (Jimenez-Sanchez et al. 2014. Neuropsychopharmacology 39:2673). NR2B NAM described to date have exhibited drawbacks with regard to their receptor pharmacology and/or to other drug properties which have limited potential use in human drug therapy (Taylor, et al., 2006, Clin Pharmacokinet. 45: 989; Addy et al. 2009 J of Clinical Pharmacology 49:856)).

WO2016/29146 discloses compounds of formula (I)

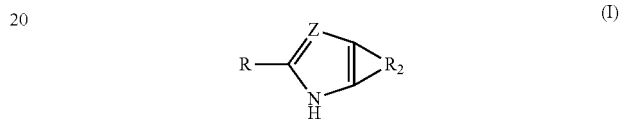

that are inhibitors of methionyl-tRNA synthetase (MetRS) being useful as antibiotics. Formula (I) in WO2016/29146 encompasses the specific examples 1734, 1744, 1745, 1757 1758, 1785 and 1790 which exhibit a benzimidazole or imidazopyridine substructure.

The compounds of the present invention have surprisingly been found to be potent NR2B negative allosteric modulators (see table 1), whereas the specific examples 1734, 1744, 1745, 1757, 1758, 1785 and 1790 of WO2016/29146 show rather poor negative allosteric modulation of the NR2B ion channel or no activity at all (see table 2).

Further, the compounds of the present invention show good membrane permeability and low to moderate in vitro efflux (see table 3 for MDCK assay MDR1 (p-GP)). Therefore, compounds of present invention are expected to show a favorable brain penetration which is required for efficacious CNS medicaments.

The MDCK assays provide information on the potential of a compound to pass the blood brain barrier. Permeability measurements across polarized, confluent MDCK-MDR1 cell monolayers grown on permeable filter supports are used as an in vitro absorption model: apparent permeability coefficients (PE) of the compounds across the MDCK-MDR1 cell monolayers are measured (pH 7.4, 37° C.) in apical-to-basal (AB) and basal-to-apical (BA) transport direction. The AB permeability (PEAB) represents drug absorption from the blood into the brain and the BA permeability (PEBA) drug efflux from the brain back into the blood via both, passive permeability as well as active transport mechanisms mediated by efflux and uptake transporters that are expressed on the MDCK-MDR1 cells, predominantly by the overexpressed human MDR1. Identical or similar permeabilities in both transport directions indicate passive permeation, vectorial permeability points to additional active transport mechanisms. Higher PEBA than PEAB (PEBA/PEAB>5) indicates the involvement of active efflux mediated by MDR1, which might compromise the goal to achieve sufficient brain exposure. Therefore, this assay provides valuable support for selection of compounds applicable for further in vivo testing. High permeability not limited by efflux at the blood brain barrier is a favourable characteristic for compounds that are to be used for drugs acting primarily in the CNS. Consequently, to ensure high permeability at the blood brain barrier, it is highly preferred to minimize the efflux (efflux <5) at MDR1 transporter.

Further, the compounds of the present invention are metabolically stable in human liver microsomes (see table 4, metabolic stability). Therefore, compounds of the present invention are expected to have a favorable in vivo clearance and thus the desired duration of action in humans.

Stability in human liver microsomes refers to the susceptibility of compounds to biotransformation in the context of selecting and/or designing drugs with favorable pharmacokinetic properties. The primary site of metabolism for many drugs is the liver. Human liver microsomes contain the cytochrome P450s (CYPs), and thus represent a model system for studying drug metabolization in vitro Enhanced stability in human liver microsomes is associated with several advantages, including increased bioavailability and adequate half-life, which can enable lower and less frequent dosing of patients. Thus, enhanced stability in human liver microsomes is a favorable characteristic for compounds that are to be used for drugs.

Consequently, compounds of the present invention must be more viable for human use.

The objective technical problem is thus to provide potent NR2B negative allosteric modulators.

The present invention provides novel purines of formula A

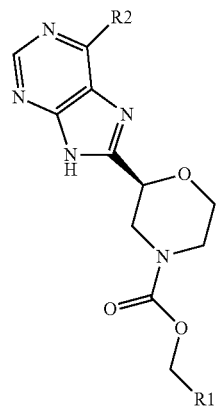

in which
R$^1$ represents phenyl which is optionally substituted with 1, 2 or 3 substituents selected from the group consisting of fluoro, chloro, methyl, ethyl, cyclopropyl, F$_2$HC—, FH$_2$C—, F$_3$C—;
R$^2$ represents hydrogen, methyl;
or a salt thereof, particularly a pharmaceutically acceptable salt thereof.

In another embodiment, in the general formula A, R$^1$ has the same meaning as defined in any of the preceding embodiments, and
R$^2$ represents hydrogen.

In another embodiment, in the general formula A, R$^1$ has the same meaning as defined in any of the preceding embodiments, and
R$^2$ represents methyl.

In another embodiment, in the general formula A, R$^2$ has the same meaning as defined in any of the preceding embodiments, and R$^1$ represents phenyl which is optionally substituted with 1, 2 or 3 substituents selected from the group consisting of fluoro, chloro, methyl, F$_2$HC—.

In another embodiment, in the general formula A, R$^2$ has the same meaning as defined in any of the preceding embodiments, and
R$^1$ represents

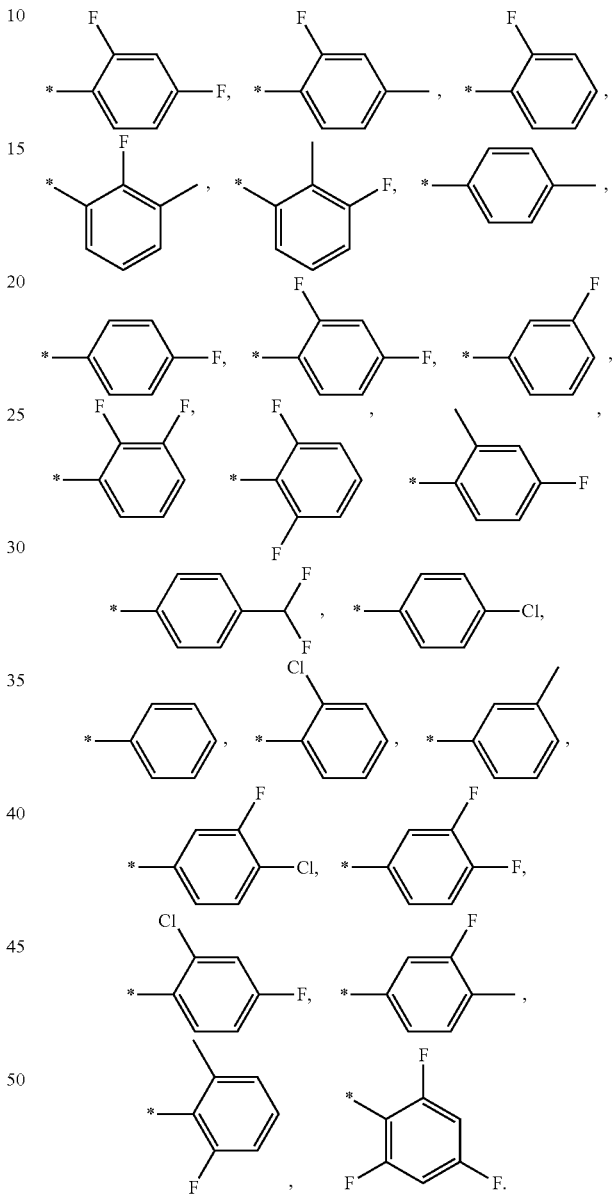

The present invention provides novel purines of general formula A that unexpectedly are potent NR2B negative allosteric modulators.

Another aspect of the invention refers to compounds according to formula A as NR2B negative allosteric modulators having appropriate membrane permeability and low to moderate in vitro efflux.

Another aspect of the invention refers to compounds according to formula A as NR2B negative allosteric modulators having high metabolic stability in human liver microsomes.

Another aspect of the invention refers to compounds according to formula A as NR2B negative allosteric modulators having appropriate membrane permeability, low to moderate in vitro efflux and high metabolic stability in human liver microsomes.

Another aspect of the invention refers to pharmaceutical compositions, containing at least one compound according to formula A optionally together with one or more inert carriers and/or diluents.

A further aspect of the present invention refers to compounds according to formula A, for the use in the prevention and/or treatment of disorders associated with NR2B negative allosteric modulators.

Another aspect of the invention refers to processes of manufacture of the compounds of the present invention.

Preparation

The following schemes shall illustrate generally how to manufacture the compounds according to general formula A and the corresponding intermediate compounds by way of example. The abbreviated substituents may be as defined above if not defined otherwise within the context of the schemes.

Scheme 1: Method A

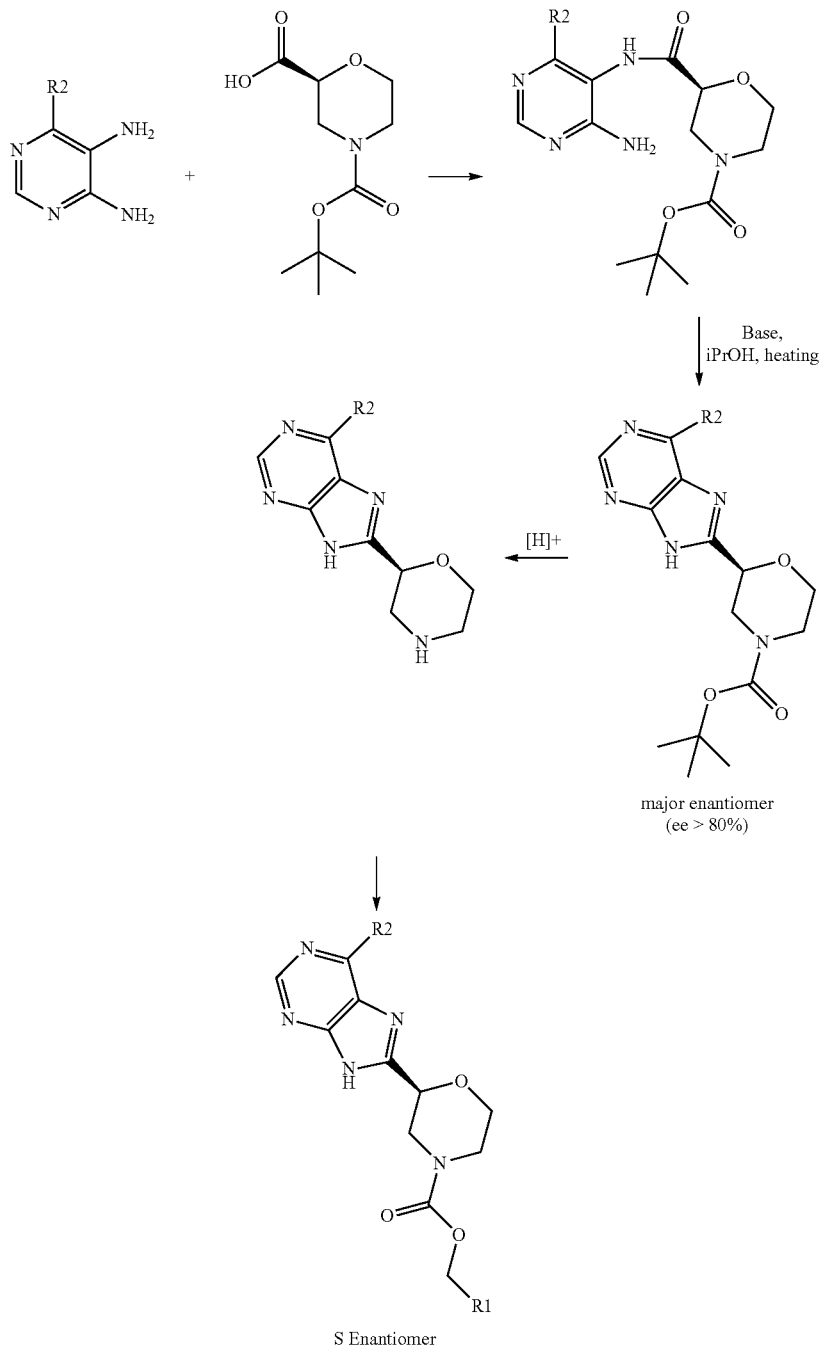

Scheme 2: Method B
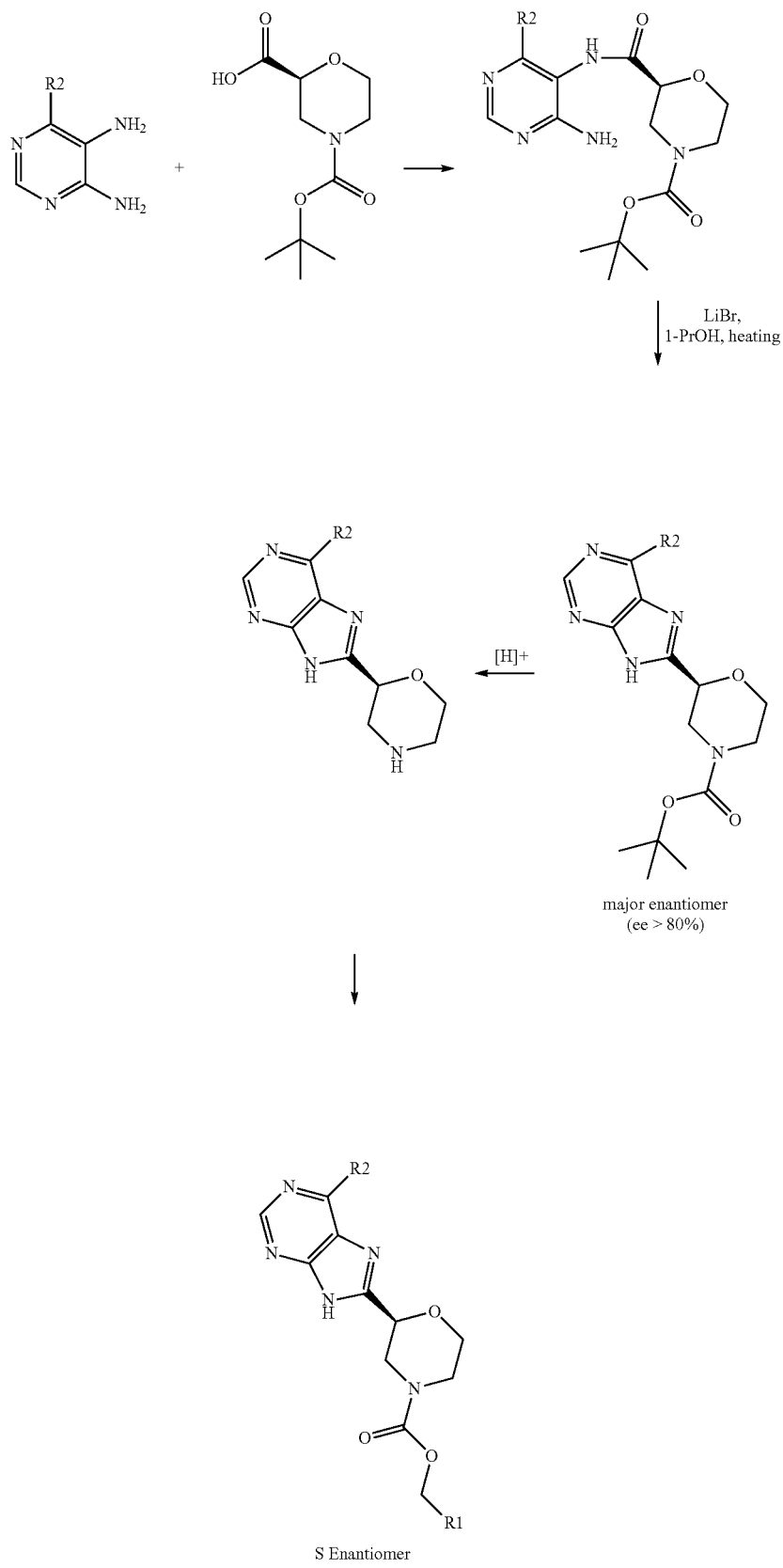
major enantiomer
(ee > 80%)
S Enantiomer

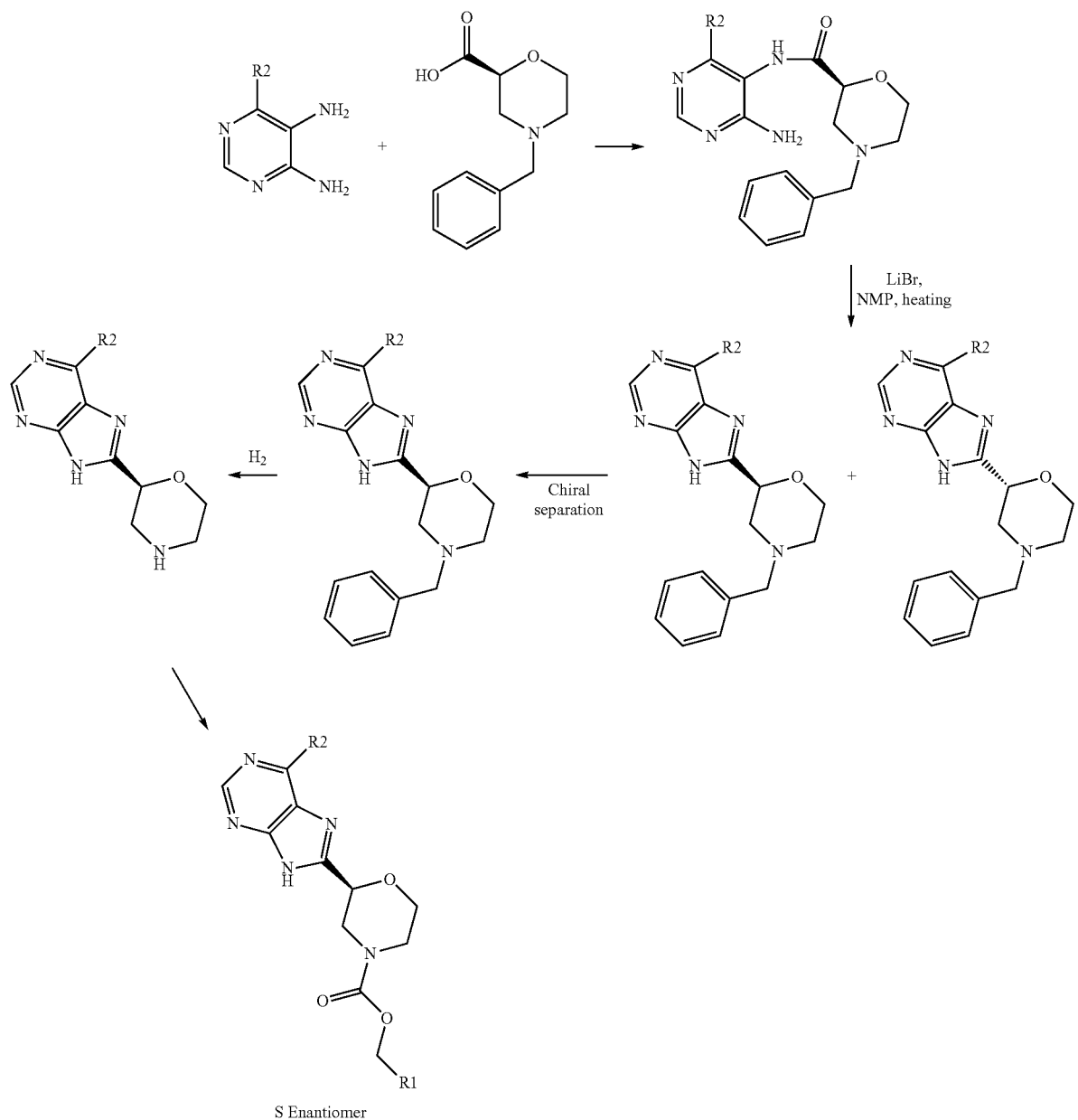

Scheme 3: Method C

S Enantiomer

Alternatively, the synthesis according to schemes 1, 2 and 3 can be performed using racemic morpholine-2,4-dicarboxylic acid 4-tert-butyl ester or 4-Benzyl-morpholine-2-carboxylic acid as starting materials.

Schemes 1, 2 and 3 can be successfully used for gram scale synthesis of the final compounds starting from 40 mmoles of the desired substituted morpholine (racemic or the S enantiomer), using an excess of the desired substituted benzyl alcohol, DIPEA (3 equivalents), the needed coupling agent such as CDI or Bis-[1,2,4]triazol-1-yl-methanone and DMF as solvent. The final compounds can be obtained with good to high enantiomeric excess; alternatively, chiral separation can be applied to obtain the pure enenantiomers.

An alternative gram scale synthesis can be performed using the corresponding morpholine (racemic or the S enantiomer; 40 mmol), TEA (2.5 equivalents), a slight excess of the required imidoylcarbonate and a 1/1 mixture $CH_3CN/THF$ (volume/volume) as solvent.

In schemes 1, 2 and 3 all substituents $R^1$ and $R^2$ have the meaning as defined for general formula A, all embodiments of the invention that directly refer thereto and specifically the meaning as defined in the claims.

General Definitions

Terms not specifically defined herein should be given the meanings that would be given to them by one skilled in the art in light of the disclosure and the context.

In case a compound of the present invention is depicted in form of a chemical name as well as a formula, the formula shall prevail in case of any discrepancy.

An asterisk may be used in sub-formulas to indicate the bond which is connected to the core molecule or to the substituent to which it is bound as defined.

The term "substituted" as used herein means that any one or more hydrogens on the designated atom is replaced with a selection from the indicated group, provided that the designated atom's viable valence number is not exceeded, and that the substitution results in a stable compound.

Stereochemistry:

Unless specifically indicated, throughout the specification and the appended claims, a given chemical formula or name shall encompass rotamers, tautomers and all stereo, optical and geometrical isomers (e.g. enantiomers, diastereoisomers, E/Z isomers etc.) and racemates thereof, as well as mixtures in different proportions of the separate enantiomers, mixtures of diastereoisomers, or mixtures of any of the foregoing forms where such isomers and enantiomers exist, as well as salts, including pharmaceutically acceptable salts thereof.

General Formula A

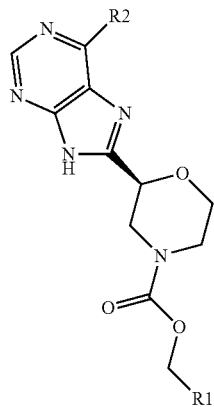

A comprises both tautomers A-1 and A-2:

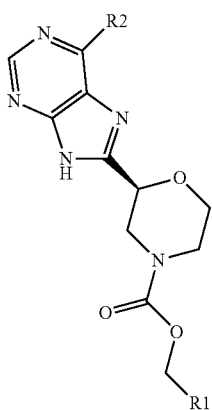

A-1

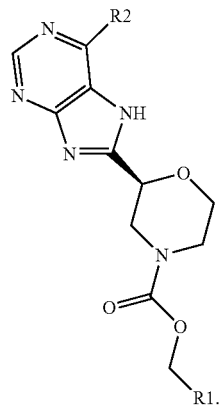

A-2

All compounds of the present invention exist in their tautomeric forms A-1 and/or A-2.

Salts:

The phrase "pharmaceutically acceptable" is employed herein to refer to those compounds, materials, compositions, and/or dosage forms which are, within the scope of sound medical judgment, suitable for use without excessive toxicity, irritation, allergic response, or other problem or complication, and commensurate with a reasonable benefit/risk ratio.

As used herein, "pharmaceutically acceptable salts" refer to derivatives of the disclosed compounds wherein the parent compound forms a salt or a complex with an acid or a base.

Examples for acids forming a pharmaceutically acceptable salt with a parent compound containing a basic moiety include mineral or organic acids such as benzenesulfonic acid, benzoic acid, citric acid, ethanesulfonic acid, fumaric acid, gentisic acid, hydrobromic acid, hydrochloric acid, maleic acid, malic acid, malonic acid, mandelic acid, methanesulfonic acid, 4-methyl-benzenesulfonic acid, phosphoric acid, salicylic acid, succinic acid, sulfuric acid or tartaric acid.

Examples for cations and bases forming a pharmaceutically acceptable salt with a parent compound containing an acidic moiety include $Na^+$, $K^+$, $Ca^{2+}$, $Mg^{2+}$, $NH_4^+$, L-arginine, 2,2'-iminobisethanol, L-lysine, N-methyl-D-glucamine or tris(hydroxymethyl)-aminomethane.

The pharmaceutically acceptable salts of the present invention can be synthesized from the parent compound which contains a basic or acidic moiety by conventional chemical methods. Generally, such salts can be prepared by reacting the free acid or base forms of these compounds with a sufficient amount of the appropriate base or acid in water or in an organic diluent like ether, ethyl acetate, ethanol, isopropanol, or acetonitrile, or a mixture thereof. Salts of other acids than those mentioned above which for example are useful for purifying or isolating the compounds of the present invention (e.g. trifluoroacetate salts) also comprise a part of the invention.

Biological Assays and Data

List of Abbreviations

DMEM Dulbecco's Modified Eagle's Medium
FBS fetal Bovine Serum
FLIPR fluorometric imaging plate reader HEK293 cell line derived from human embryonic kidney cells
HEPES hydroxyethyl-piperazineethane-sulfonic acid buffer
MDCK Madin-Darby canine kidney
MDR1 Multi drug resistance protein 1
p-GP p-Glycoprotein
In-Vitro Effect:
Determination of In Vitro Pharmacological Activity The activity of the compounds of the invention may be demonstrated using the following in vitro NMDA NR1/NR2b cell assays:

Method:

A human HEK293 cell line with tetracyclin-inducible expression of NMDA NR1/NR2B receptor was used as a test system for compound efficacy and potency. The cell line was purchased from ChanTest, Catalog #CT6121. Compound activity was determined by measuring the effect of compounds on intracellular calcium concentration induced by glycine/glutamate agonism in a FLIPRtetra system (Molecular Devices).

Cell Culture:

The cells were obtained as frozen cells in cryo-vials and stored until use at −150° C. Cells were grown in culture medium (DMEM/F12, 10% FBS, 5 µg/mL Blasticidin, 150 µg/mL Zeozin, 500 µg/mL Geneticin). It is important that density does not exceed 80% confluence. For sub-culturing the cells were detached from flasks by Versene. For the assay, cells were detached, washed twice with induction medium (DMEM/F12 without glutamine, 10% FBS, 2 µg/mL Tetracycline, 2 mM Ketamine) and seeded to 384 well pure coat amine plates (BD 359324, 50000 cells per well in 50 µl) 48 h prior to assay in induction medium.

Compound Preparation

The test compounds were dissolved in 100% DMSO at a concentration of 10 mM and in a first step diluted in DMSO to a concentration of 5 mM, followed by serial dilution steps in 100% DMSO. Dilution factor and number of dilution steps may vary according to needs. Typically 8 different concentrations by 1:5 dilutions were prepared in duplicate, further intermediate dilutions (1:37.5) of the substances were carried out with aqueous assay buffer (137 mM NaCl, 4 mM KCl, 1.8 mM CaCl, 10 mM HEPES, 10 mM Glucose, pH 7.4) resulting in a compound concentration 3 times above the final test concentration and DMSO at 2.7% resulting in 0.9% final DMSO concentration in the assay.

FLIPR Assay:

At the assay day cells were washed 3× with assay buffer, 10 µL buffer remained in the wells after washing. 10 µL Ca kit loading buffer (AAT Bioquest) was added to the cells and the plates were incubated with lid for 60 minutes at r.t. 20 µl assay buffer containing 60 µM glycine (20 µM final) and 3 µM glutamate (1 µM final) was added to column 1-23. Fluorescence (indicating the calcium influx as a result of the NR1/NR2B ion channel activation) was read on the FLIPRtetra device for 60 seconds to monitor the glutamate induced effects. After 2 minutes 20 µL of compound or controls (row 1-22) in assay buffer were carefully added to the wells. Fluorescence was read on the FLIPR tetra device for additional 6 minutes to monitor the compound induced effects after activation by agonists. The average of 2 measurements at 5 minutes and 5 mM 10 seconds after compound addition is calculated and further used for IC50 calculations. Each assay microtiter plate contained wells (in column 23 or 24) with DMSO controls instead of compound as controls for glycine/glutamate induced fluorescence (high controls) and wells with 1 µM of a reference NR2b NAM as low controls (Compound 22; reference: Layton, Mark E et al, ACS Chemical Neuroscience 2011, 2(7), 352-362).

Data Evaluation and Calculation:

The output file of the reader contains the well number and measured average fluorescence units. For data evaluation and calculation, the measurement of the low control was set as 0% control and the measurement of the high control was set as 100% control. The IC50 values were calculated using the standard 4 parameter logistic regression formula. Calculation: $[y=(a-d)/(1+(x/c)^b)+d]$, a=low value, d=high value; x=conc M; c=IC50 M; b=slope.

NR2B negative allosteric modulators covered by general structure A and exhibiting a low $IC_{50}$ value are preferred.

TABLE 1

In vitro affinity of the compounds of the present invention as obtained in the FLIPR assay

| Example number | IC50 [nM] |
|---|---|
| 2 | 427 |
| 6 | 83 |
| 7 | 385 |
| 8 | 83 |
| 9 | 520 |
| 10 | 67 |
| 11 | 637 |
| 13 | 107 |
| 14 | 102 |
| 16 | 295 |
| 17 | 74 |
| 18 | 60 |
| 19 | 111 |
| 20 | 234 |
| 21 | 150 |
| 24 | 45 |
| 25 | 113 |
| 26 | 114 |
| 28 | 88 |
| 29 | 322 |
| 30 | 314 |
| 31 | 520 |
| 32 | 90 |
| 34 | 100 |
| 36 | 49 |
| 37 | 118 |
| 38 | 84 |

TABLE 2

In vitro affinity of the closest prior art compounds (examples 1734, 1744, 1745, 1757, 1758, 1785 and 1790 in WO2016/29146) as obtained in the same FLIPR assay as compounds in table 1

| Example number in WO2016/29146 | IC50 [nM] |
|---|---|
| 1734 | >8885 |
| 1744 | >8889 |
| 1745 | >8898 |
| 1757 | >8900 |
| 1758 | >8884 |
| 1785 | 6200 |
| 1790 | >8887 |

MDCK Assay MDR-1 (p-GP)

Apparent permeability coefficients (Papp) of the compounds across the MDCK-MDR1 monolayers (MDCKII cells transfected with human MDR1 cDNA expression plasmid) are measured in apical-to-basal (AB) and basal-to-apical (BA) direction.

MDCK-MDR1 cells ($6 \times 10^5$ cells/cm$^2$) are seeded on filter inserts (Corning, Transwell, polycarbonate, 0.4 µm pore size) and cultured for 9 to 10 days. Compounds dissolved in DMSO stock solution (1-20 mM) are diluted with HTP-4 aqueous buffer (128.13 mM NaCl, 5.36 mM KCl, 1 mM MgSO4, 1.8 mM CaCl2, 4.17 mM NaHCO$_3$, 1.19 mM Na2HPO4, 0.41 mM NaH2PO4, 15 mM HEPES, 20 mM glucose, pH 7.4) supplemented with 0.25% BSA to prepare the transport solutions (final concentration: 1 or 10 µM, final DMSO<=0.5%). The transport solution is applied to the apical or basolateral donor side for measuring A-B or B-A permeability, respectively. The receiver side contains HTP-4 buffer supplemented with 0.25% BSA. Samples are collected at the start and end of experiment from the donor and at various time intervals for up to 2 hours also from the receiver side for concentration measurement by HPLC-MS/MS. Sampled receiver volumes are replaced with fresh receiver solution. Efflux ratio is calculated dividing the Papp (b-a) values by the Papp (a-b) values. Results are shown in table 3.

TABLE 3

| Ex. | Papp (a-b) mean [10−6 cm/s] | efflux ratio |
| --- | --- | --- |
| 2 | 40 | 1.6 |
| 6 | 36 | 1.6 |
| 7 | 24 | 2.3 |
| 8 | 31 | 1.5 |
| 9 | 42 | 1.0 |
| 10 | 41 | 1.6 |
| 11 | 17 | 3.3 |
| 13 | 23 | 2.6 |
| 14 | 32 | 1.6 |
| 16 | 22 | 1.8 |
| 17 | 36 | 1.0 |
| 18 | 46 | 1.4 |
| 19 | 60 | 0.6 |
| 20 | 25 | 2.1 |
| 21 | 28 | 1.9 |
| 24 | 14 | 4.0 |
| 25 | 26 | 2.4 |
| 26 | 42 | 1.2 |
| 28 | 39 | 1.2 |
| 29 | 72 | 0.5 |
| 30 | 69 | 0.5 |
| 31 | 38 | 1.0 |
| 32 | 21 | 2.5 |
| 34 | 53 | 0.6 |
| 36 | 51 | 0.7 |
| 37 | 38 | 1.2 |
| 38 | 27 | 2.3 |

The experimental results above show that compounds of the present invention are potent NR2B NAMs having good membrane permeability and low to moderate in vitro efflux.

Metabolic Stability

The metabolic degradation of the test compound was assayed at 37° C. with pooled human liver microsomes. The final incubation volume of 60 µl per time point contains TRIS buffer pH 7.6 at room temperature (0.1 M), magnesium chloride (5 mM aqueous solution), microsomal protein (1 mg/mL for human) and the test compound at a final concentration of 1 µM. Following a short preincubation period at 37° C., the reactions were initiated by addition of betanicotinamide adenine dinucleotide phosphate, reduced form (NADPH, 1 mM), and terminated by transferring an aliquot into solvent after different time points. After centrifugation (10000 g, 5 min), an aliquot of the supernatant was assayed by LC-MS/MS for the amount of parent compound. The half-life was determined by the slope of the semi-logarithmic plot of the concentration-time profile. Results are shown in Table 4.

TABLE 4

| Ex. | Half-life - t½ [min] human liver microsomes |
| --- | --- |
| 2 | >130 |
| 6 | 78 |
| 7 | >130 |
| 8 | 12 |
| 9 | 25 |
| 10 | 39 |
| 11 | >130 |
| 13 | >130 |
| 14 | >130 |
| 16 | >130 |
| 17 | >130 |
| 18 | >130 |
| 19 | 86 |
| 20 | 50 |
| 21 | 86 |
| 24 | >130 |
| 25 | >130 |
| 26 | >130 |
| 28 | 48 |
| 29 | 25 |
| 30 | >130 |
| 31 | >130 |
| 32 | 37 |
| 34 | 24 |
| 36 | 20 |
| 37 | 17 |
| 38 | >130 |

The present invention provides compounds according to formula A that unexpectedly result in a favorable combination of the following key parameters:

1) NR2B negative allosteric modulation,
2) favorable stability in human liver microsomes, and
3) moderate to low in vitro efflux at MDR1 transporter.

Pharmaceutical Composition

Suitable preparations for administering the compounds of the present invention will be apparent to those with ordinary skill in the art and include for example tablets, pills, capsules, suppositories, lozenges, troches, solutions, syrups, elixirs, sachets, injectables, inhalatives, powders, etc. The content of the pharmaceutically active compound(s) may vary in the range from 0.1 to 95 wt.-%, preferably 5.0 to 90 wt.-% of the composition as a whole.

Suitable tablets may be obtained, for example, by mixing a compound of the present invention with known excipients, for example inert diluents, carriers, disintegrants, adjuvants, surfactants, binders and/or lubricants and pressing the resulting mixture to form tablets.

Use in Treatment/Method of Use

Human therapeutic applications of NR2B NAM have been summarized in reviews by Traynelis et al. (Traynelis et al., Pharmacology Reviews, 2010, 62:405), Beinat et al. (Beinat et al., Current Medicinal Chemistry, 2010, 17:4166) and Mony et al. (Mony et al., British J. Pharmacology, 2009, 157:1301).

The present invention relates to compounds which are useful in the treatment of psychiatric disorders, diseases and conditions wherein negative allosteric modulation of NR2B is of therapeutic benefit, including: (1) mood disorders and mood affective disorders; (2) schizophrenia spectrum disorders; (3) neurotic, stress-related and somatoform disorders including anxiety disorders; (4) disorders of psychological development; (5) behavioral syndromes associated with physiological disturbances and physical factors; (6) substance-related and addictive disorders; (7) disease associated with symptoms of negative and positive valence.

In view of their pharmacological effect, compounds of the present invention are suitable for use in the treatment of a disorder, disease or condition selected from the list consisting of (1) Treatment of Mood Disorders and Mood Affective Disorders Including Bipolar Disorder I depressed, hypomanic, manic and mixed form; bipolar disorder II; depressive disorders, such as single depressive episode or recurrent major depressive disorder, minor depressive disorder, depressive disorder with postpartum onset, depressive disorders with psychotic symptoms; major depressive disorder with or without concomitant anxious distress, mixed features, melancholic features, atypical features, mood-congruent psychotic features, mood-incongruent psychotic features, catatonia.

(2) treatment of mood disorders belonging to the schizophrenia spectrum and other psychotic disorders including schizophrenia and schizoaffective disorder with associated negative and cognitive symptoms.

(3) treatment of disorders belonging to the neurotic, stress-related and somatoform disorders including anxiety disorders, general anxiety disorder, panic disorder with or without agoraphobia, specific phobia, social phobia, chronic anxiety disorders; obsessive compulsive disorder; reaction to sever stress and adjustment disorders, such as post-traumatic stress disorder; other neurotic disorders such as depersonalisation-derealisation syndrome.

(4) treatment of disorders of psychological development including pervasive developmental disorders, including Asperger's syndrome and Rett's syndrome, autistic disorders, childhood autism and overactive disorder associated with mental retardation and stereotyped movements, specific developmental disorder of motor function, specific developmental disorders of scholastic skills, attention deficit/hyperactivity disorder.

(5) treatment of behavioral syndromes associated with physiological disturbances and physical factors including mental and behavioural disorders associated with the puerperium, including postnatal and postpartum depression; eating disorders, including anorexia nervosa and bulimia nervosa and other impulse control disorders.

(6) treatment of disorders of substance-related and addictive disorders, which are substance use disorders induced by alcohol, cannabis, hallucinogen, stimulant, hypnotic, tobacco.

(7) treatment of disease associated with symptoms of negative and positive valence including anhedonia, sustained threat and loss, suicidal ideation.

As used herein, unless otherwise noted, the terms "treating", "treatment" shall include the management and care of a human subject or human patient for the purpose of combating a disease, condition, or disorder and includes the administration of a compound of the present invention to prevent the onset of the symptoms or complications, alleviate the symptoms or complications, or eliminate the disease, condition, or disorder.

As used herein, unless otherwise noted, the term "prevention" shall include (a) reduction in the frequency of one or more symptoms; (b) reduction in the severity of one or more symptoms; (c) the delay or avoidance of the development of additional symptoms; and/or (d) delay or avoidance of the development of the disorder or condition.

According to another aspect, the present invention provides a compound of formula A or a pharmaceutically acceptable salt thereof for use in the treatment and/or prevention of the above mentioned conditions.

According to another aspect, the present invention provides a compound of formula A according to any one of the preceding aspects characterized in that the compound of formula A is used in addition to behavioural therapy, TMS (transcranial magnetic stimulation), ECT (electroconvulsive therapy) and other therapies.

Combination Therapy

Compounds according to the present invention can be combined with other treatment options known to be used in the art in connection with a treatment of any of the indications the treatment of which is in the focus of the present invention.

According to another aspect, the present invention provides a compound of formula A according to any one of the preceding aspects characterized in that the compound of formula A is administered in addition to treatment with one or more antidepressant selected from the list consisting of duloxetine, escitalopram, bupropion, venlafaxine, desvenlafaxine, sertraline, paroxetine, fluoxetine, vortioxetine, mirtazapine, citalopram, vilazodone, trazodone, amitriptyline, clomipramine, agomelatine, levomilnacipran, lithium, doxepin, nortriptyline. The term "antidepressant" shall mean any pharmaceutical agent or drug which can be used to treat depression or diseases associated with depressive symptoms. According to another aspect, the present invention provides a compound of formula A according to any one of the preceding aspects characterized in that the compound of formula A is administered in addition to treatment with one or more antipsychotic selected from the list consisting of aripiprazole, paliperidone palmitate, lurasidone, quetiapine, risperidone, olanzapine, paliperidone, brexpiprazole, clozapine, asenapine, chlorpromazine, haloperidol, cariprazine, ziprasidone, amisulpride, iloperidone, fluphenazine, blonanserin, aripiprazole lauroxil. The term "antipsychotic" shall mean any pharmaceutical agent or drug which can be used to treat diseases associated with psychotic or depressive symptoms.

According to another aspect, the present invention provides a compound of formula A according to any one of the preceding aspects characterized in that the compound of formula A is administered in addition to treatment with one or more psychostimulant selected from the list consisting of lisdexamfetamine, methylphenidate, amfetamine, dexamfetamine, dexmethylphenidate, armodafinil, modafinil. The term "psychostimulant" shall mean any pharmaceutical agent or drug which can be used to treat diseases like mood disorders, or impulse control disorders.

According to another aspect, the present invention provides a compound of formula A according to any one of the preceding aspects characterized in that the compound of formula A is administered in addition to treatment with nootropics selected from the list consisting of oxiracetam, piracetam, or the natural product St John's-wort.

According to another aspect, the present invention provides a compound of formula A which is administered in addition to treatment with one or more antidepressant, antipsychotic, psychostimulant, nootropics or natural product according to any one of the preceding aspects characterized in that the combination of compound of formula A and one or more antidepressant, antipsychotic, psychostimulant, nootropics or natural product is used in addition to behavioural therapy, TMS (transcranial magnetic stimulation), ECT (electroconvulsive therapy) and other therapies.

EXPERIMENTAL SECTION

Abbreviations

ACN acetonitrile
Alox B Aluminium oxide, basic

APCI Atmospheric pressure chemical ionization
Boc tert-butyloxycarbonyl
CDI 1,1'-carbonyldiimidazole
CO2 Carbon Dioxide
d day
DA Diode Array
DAD Diode Array Detector
DCM dichloromethane
DIPE diisopropylether
DIPEA diisopropylethylamine
DMF dimethylformamide
ee, e.e. enantiomeric excess
ELSD Evaporative Light Scattering Detector
ESI electrospray ionization (in MS)
EtOAc ethylacetate
EtOH ethanol
Exp. example
h hour(s)
HATU O-(7-azabenzotriazol-1-yl)-N,N,N',N'-tetramethyl-uronium-hexafluorophosphate
HPLC high performance liquid chromatography
HPLC-MS coupled high performance liquid chromatography-mass spectrometry
IPA Isopropanol
M molar (mol/L)
MeOH methanol
min minute(s)
MS mass spectrometry
MW molecular weight
$NH_3$ ammonia
NMP N-Methyl-2-pyrrolidone
PSI Pound per square inch
QDa Quadrupole Dalton
rt room temperature
$R_t$ retention time
$scCO2$ supercritical $CO_2$
Sol Solvent
soln Solution
solv solvent
TBTU O-(benzotriazol-1-yl)-N,N,N',N'-tetramethyluronium tetrafluoroborate
TEA triethylamine
TFA trifluoroacetic acid
THF tetrahydrofuran
TLC thin-layer chromatography
SFC Supercritical fluid chromatography General Analytics All of the following reactions were carried out using commercial grade reagents and solvents. NMR spectra were recorded on a Bruker AVANCE IIIHD 400 MHz instrument using TopSpin 3.2 p16 software. Chemical shifts are given in parts per million (ppm) downfield from internal reference trimethylsilane in δ units. Selected data are reported in the following manner: chemical shift, multiplicity, coupling constants (J), integration. Analytical thin-layer chromatography (TLC) was carried out using Merck silica gel 60 F254 plates. All compounds were visualized as single spots using short wave UV light. Low resolution mass spectra were obtained using a liquid chromatography mass spectrometer (LCMS) that consisted of an Agilent 1100 series LC coupled to a Agilent 6130 quadrupole mass spectrometer (electrospray positive ionization).

Methods:

For solvent mixtures used for HPLC-MS methods and Chiral SFC analytical methods, % solvent are given as volume percent of the corresponding solvent.

HPLC-MS Methods:

| Method 1 | |
|---|---|
| Method Name: | Z003_S05 |
| Device description: | Agilent 1200 with DA- and MS-Detector |
| Column: | XBridge C18_3.0 × 30 mm_2.5 μm |
| Column producer: | Waters |
| Description: | |

| Gradient/Solvent Time [min] | % Sol [Water 0.1% $NH_3$] | % Sol [Acetonitrile] | Flow [ml/min] | Temp [° C.] | Back pressure [PSI] |
|---|---|---|---|---|---|
| 0.0 | 95.0 | 5.0 | 2.2 | 60.0 | |
| 0.2 | 95.0 | 5.0 | 2.2 | 60.0 | |
| 1.2 | 0.0 | 100.0 | 2.2 | 60.0 | |
| 1.25 | 0.0 | 100.0 | 3.0 | 60.0 | |
| 1.4 | 0.0 | 100.0 | 3.0 | 60.0 | |

| Method 2 | |
|---|---|
| Method Name: | Z011_S03 |
| Device description: | Agilent 1200 with DA- and MS-Detector |
| Column: | XBridge C18_3.0 × 30 mm_2.5 μm |
| Column producer: | Waters |
| Description: | |

| Gradient/Solvent Time [min] | % Sol [Water 0.1% $NH_3$] | % Sol [Acetonitrile] | Flow [ml/min] | Temp [° C.] | Back pressure [PSI] |
|---|---|---|---|---|---|
| 0.0 | 97.0 | 3.0 | 2.2 | 60.0 | |
| 0.2 | 97.0 | 3.0 | 2.2 | 60.0 | |
| 1.2 | 0.0 | 100.0 | 2.2 | 60.0 | |

| \multicolumn{5}{c}{Method 2} |
| --- | --- | --- | --- | --- |
| 1.25 | 0.0 | 100.0 | 3.0 | 60.0 |
| 1.4 | 0.0 | 100.0 | 3.0 | 60.0 |

| \multicolumn{5}{c}{Method 3} | |
| --- | --- |
| Method Name: | Z018_S04 |
| Device description: | Agilent 1200 with DA- and MS-Detector |
| Column: | Sunfire C18_3.0 × 30 mm_2.5 μm |
| Column producer: | Waters |
| Description: | |

| Gradient/Solvent Time [min] | % Sol [Water 0.1% TFA] | % Sol [Acetonitrile] | Flow [ml/min] | Temp [° C.] | Back pressure [PSI] |
| --- | --- | --- | --- | --- | --- |
| 0.0 | 97.0 | 3.0 | 2.2 | 60.0 | |
| 0.2 | 97.0 | 3.0 | 2.2 | 60.0 | |
| 1.2 | 0.0 | 100.0 | 2.2 | 60.0 | |
| 1.25 | 0.0 | 100.0 | 3.0 | 60.0 | |
| 1.4 | 0.0 | 100.0 | 3.0 | 60.0 | |

| \multicolumn{2}{c}{Method 5} |
| --- | --- |
| Method Name: | 004_CA02 |
| Device description: | Waters Acquity, QDa Detector |
| Column: | XBridge C18_3.0 × 30 mm_2.5 μm |
| Column producer: | Waters |
| Description: | |

| Gradient/Solvent Time [min] | % Sol [Water 0.1% TFA] | % Sol [Acetonitrile] | Flow [ml/min] | Temp [° C.] | Back pressure [PSI] |
| --- | --- | --- | --- | --- | --- |
| 0.0 | 95.0 | 5.0 | 1.5 | 60.0 | |
| 1.3 | 0.0 | 100.0 | 1.5 | 60.0 | |
| 1.5 | 0.0 | 100.0 | 1.5 | 60.0 | |
| 1.6 | 95.0 | 5.0 | 1.5 | 60.0 | |

| \multicolumn{2}{c}{Method 6} |
| --- | --- |
| Method Name: | 004_CA11 |
| Device description: | Waters Acquity, QDa Detector |
| Column: | XBridge C18_3.0 × 30 mm_2.5 μm |
| Column producer: | Waters |
| Description: | |

| Gradient/Solvent Time [min] | % Sol [Water 0.1% TFA] | % Sol [Acetonitrile] | Flow [ml/min] | Temp [° C.] | Back pressure [PSI] |
| --- | --- | --- | --- | --- | --- |
| 0.0 | 95.0 | 5.0 | 1.5 | 60.0 | |
| 1.3 | 0.0 | 100.0 | 1.5 | 60.0 | |
| 1.5 | 0.0 | 100.0 | 1.5 | 60.0 | |
| 1.6 | 95.0 | 5.0 | 1.5 | 60.0 | |

Method 7

| Method Name: | 003_CA11 |
|---|---|
| Device description: | Waters Acquity, QDa Detector |
| Column: | Sunfire C18_3.0 × 30 mm_2.5 μm |
| Column producer: | Waters |
| Description: | |

| Gradient/Solvent Time [min] | % Sol [Water 0.1% TFA] | % Sol [Acetonitrile] | Flow [ml/min] | Temp [° C.] | Back pressure [PSI] |
|---|---|---|---|---|---|
| 0.0 | 95.0 | 5.0 | 1.5 | 60.0 | |
| 1.3 | 0.0 | 100.0 | 1.5 | 60.0 | |
| 1.5 | 0.0 | 100.0 | 1.5 | 60.0 | |
| 1.6 | 95.0 | 5.0 | 1.5 | 60.0 | |

Chiral SFC Analytical Methods:

Method 8
I_C4_20_MeOH_NH$_3$_001

| Method Name: | I_C4_20_MEOH_NH$_3$_001 |
|---|---|
| Device description: | Agilent 1260 SFC with DAD and ELSD |
| Column: | Lux ® Cellulose-4_4.6 × 250 mm_5 μm |
| Column producer: | Phenomenex |

| Gradient/Solvent Time [min] | % Sol [scCO2] | % Sol [MeOH 20 mM NH$_3$] | Flow [ml/min] | Temp [° C.] | Back pressure [PSI] |
|---|---|---|---|---|---|
| 0.0 | 80.0 | 20.0 | 4.0 | 40.0 | 2175.0 |
| 10.0 | 80.0 | 20.0 | 4.0 | 40.0 | 2175.0 |

Method 9
I_C4_25_MeOH_NH$_3$_001

| Method Name: | I_C4_25_MEOH_NH$_3$_001 |
|---|---|
| Device description: | Agilent 1260 SFC with DAD and ELSD |
| Column: | Lux ® Cellulose-4_4.6 × 250 mm_5 μm |
| Column producer: | Phenomenex |

| Gradient/Solvent Time [min] | % Sol [scCO2] | % Sol [MeOH 20 mM NH$_3$] | Flow [ml/min] | Temp [° C.] | Back pressure [PSI] |
|---|---|---|---|---|---|
| 0.0 | 75.0 | 25.0 | 4.0 | 40.0 | 2175.0 |
| 10.0 | 75.0 | 25.0 | 4.0 | 40.0 | 2175.0 |

Method 10: I_IB_25_IPA_NH$_3$_001

| Method Name: | I_IB_25_IPA_NH$_3$_001 |
|---|---|
| Device description: | Agilent 1260 SFC with DAD and MS |
| Column: | Chiralpak ® IB_4.6 × 250 mm_5 μm |
| Column producer: | Daicel |

| Gradient/Solvent Time [min] | % Sol [scCO2] | % Sol [IPA 20 mM NH$_3$] | Flow [ml/min] | Temp [° C.] | Back pressure [PSI] |
|---|---|---|---|---|---|
| 0.0 | 75.0 | 25.0 | 4.0 | 40.0 | 2175.0 |
| 10.0 | 75.0 | 25.0 | 4.0 | 40.0 | 2175.0 |

Method 11: I_IC_25_MEOH_NH$_3$_001

| Method Name: | I_IC_25_MEOH_NH$_3$_001 |
|---|---|
| Device description: | Agilent 1260 SFC with DAD and ELSD |
| Column: | Chiralpak ® IC_4.6 × 250 mm_5 μm |
| Column producer: | Daicel |

| Gradient/Solvent Time [min] | % Sol [scCO2] | % Sol [MeOH 20 mM NH$_3$] | Flow [ml/min] | Temp [° C.] | Back pressure [PSI] |
|---|---|---|---|---|---|
| 0.0 | 75.0 | 25.0 | 4.0 | 40.0 | 2175.0 |
| 10.0 | 75.0 | 25.0 | 4.0 | 40.0 | 2175.0 |

Method 12: I_IG_35_MEOH_NH$_3$_001

| Method Name: | I_IG_35_MEOH_NH$_3$_001 |
|---|---|
| Device description: | Agilent 1260 SFC with DAD and MS |
| Column: | Chiralpak ®-IG_4.6 × 250 mm_5 μm |
| Column producer: | Daicel |

| Gradient/Solvent Time [min] | % Sol [scCO2] | % Sol [EtOH 20 mM NH$_3$] | Flow [ml/min] | Temp [° C.] | Back pressure [PSI] |
|---|---|---|---|---|---|
| 0.0 | 65.0 | 35.0 | 4.0 | 40.0 | 2175.0 |
| 10.0 | 65.0 | 35.0 | 4.0 | 40.0 | 2175.0 |

Method 13: I_SA_20_MEOH_NH$_3$_001

| Method Name: | I_SA_20_MEOH_NH$_3$_001 |
|---|---|
| Device description: | Agilent 1260 SFC with DAD and MS |
| Column: | CHIRAL ART ® Amylose SA_4.6 × 250 mm_5 μm |
| Column producer: | YMC |

| Gradient/Solvent Time [min] | % Sol [scCO2] | % Sol [MeOH 20 mM NH$_3$] | Flow [ml/min] | Temp [° C.] | Back pressure [PSI] |
|---|---|---|---|---|---|
| 0.0 | 80.0 | 20.0 | 4.0 | 40.0 | 2175.0 |
| 10.0 | 80.0 | 20.0 | 4.0 | 40.0 | 2175.0 |

| Method 14: I_SA_25_MEOH_NH3_001 | |
| --- | --- |
| Method Name: | I_SA_25_MEOH_NH3_001 |
| Device description: | Agilent 1260 SFC with DAD and MS |
| Column: | CHIRAL ART ® Amylose SA_4.6 × 250 mm_5 μm |
| Column producer: | YMC |

| Gradient/Solvent Time [min] | % Sol [scCO2] | % Sol [MeOH 20 mM NH3] | Flow [ml/min] | Temp [° C.] | Back pressure [PSI] |
| --- | --- | --- | --- | --- | --- |
| 0.0 | 75.0 | 25.0 | 4.0 | 40.0 | 2175.0 |
| 10.0 | 75.0 | 25.0 | 4.0 | 40.0 | 2175.0 |

Preparation of Intermediates

Example 1b

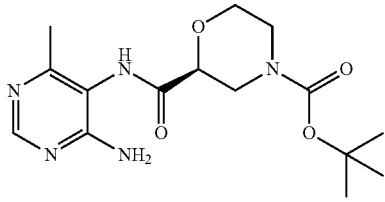 [SMILES: Cc1ncnc(N)c1NC(=O)[C@@H]1CN(C(=O)OC(C)(C)C)CCO1]

S-Morpholine-2,4-dicarboxylic acid 4-tertbutylester (13.00 g, 56.4 mmol) and 6-Methylpyrimidine-4,5-diamine (10 g, content 70%; 56.4 mmol) were dissolved in EtOAc (200 ml); the temperature was lowered to 0° C. before the addition of TEA (19.65 ml; 140.97 mmol) followed by 1-Propanephosphonic acid (50% soln in EtOAc; 39.87 ml; 67.66 mmol) added dropwise over 1 hour. The reaction mixture was stirred 1.5 h at room temperature before the work-up: 400 ml of DCM were added followed by 100 ml of NaHCO3 (5% aqueous soln.); the phases were separated and the organic phase dried over Na2SO4; the crude obtained after evaporation of the solvents was purified by flash chromatography using a mixture EtOAc/MeOH 80/20. Obtained 5.78 g of the desired compound.

| HPLC-MS; Method: Z011_S03; Rt [min]: 0.76 | MS: 338 (M + H)+ |
| --- | --- |
| Chiral SFC; Method: I_C4_20_MEOH_NH3_001; | Rt [min]: 3.31 min; e.e. 100% |

Example 1c

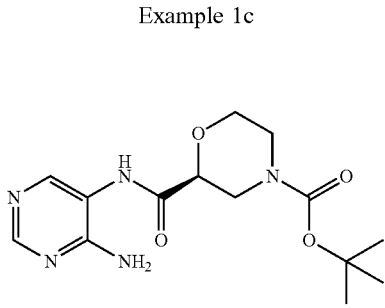

S-Morpholine-2,4-dicarboxylic acid 4-tertbutylester (25.0 g, 108 mmol) was dissolved in THF (400 ml). Then TBTU (38.2 g, 119 mmol) was added, followed by Pyrimidine-4,5-diamine hydrochloride (15.9 g, 108 mmol, CAS No. 97846-32-7) and TEA (30.1 ml, 216 mmol). The reaction mixture was stirred 20 h at room temperature before the work-up: The reaction mixture was filtered and the filtrate was concentrated in vacuo. The residue was treated with 150 mL H2O and stirred for 30 min. The obtained precipitate was filtered off, washed with H2O and dried at 55° C. in the oven. Obtained 34.3 g of the desired product.

| Chiral SFC; Method: I_C4_20_MEOH_NH3_001; Rt [min]: 3.31 min | MS: 324 (M + H)+ ee: 100% |
| --- | --- |

Example 1f

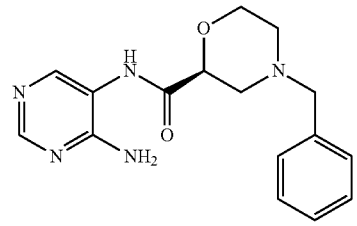 [SMILES: Nc1ncncc1NC(=O)[C@@H]1CN(Cc2ccccc2)CCO1]

Pyrimidine-4,5-diamine hydrochloride (5.00 g, 34.1 mmol) and (S)-4-Benzyl-morpholine-2-carboxylic acid (7.75 g, 35.0 mmol) were dissolved in DMF (150 ml) and DIPEA (15 ml, 87.8 mmol). Then HATU (13.3 g, 35.0 mmol) was added and the reaction mixture was stirred at room temperature over the weekend. Work-up: The reaction mixture was diluted with 25 ml K2CO3 solution (2M in water), filtered over Alox B and washed with a mixture of DMF/MeOH. The crude was separated via column chromatography (eluent: DCM/MeOH/NH3 9/1/0.1, volume/volume/volume). Obtained 8.81 g of the desired product.

| HPLC-MS; Method: Z011_S03; Rt [min]: 0.79 | MS: 314 (M + H)+ |
| --- | --- |
| Chiral SFC; Method: I_IB_25_IPA_NH3_001 | Rt [min]: 3.23; ee 99.1% |

Example 2b

Method a (According to Scheme 1)

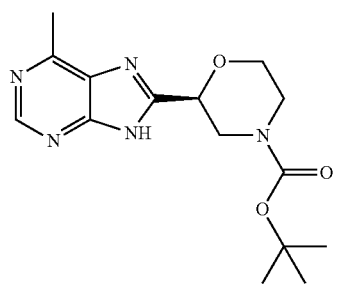 [SMILES: Cc1ncnc2[nH]c([C@@H]3CN(C(=O)OC(C)(C)C)CCO3)nc12]

A mixture of example 1b (4.30 g, 12.75 mmol), potassium carbonate (1.76 g, 12.75 mmol) and isopropanol (300 ml)

was stirred for 22 h at 80° C. The precipitate was filtered off, washed with isopropanol and the filtrate was concentrated in vacuo. The residue was dried overnight. Obtained 4.06 g of the desired compound used as such in the next step.

| HPLC-MS; Method: Z011_S03; R$_t$ [min]: 0.59 | MS: 320 (M + H)$^+$ |
|---|---|
| Chiral SFC; Method: I_IG_35_MEOH_NH$_3$_001 | R$_t$ [min]: 3.05; ee: 94.2% |

Example 2b

Method B (According to Scheme 2)

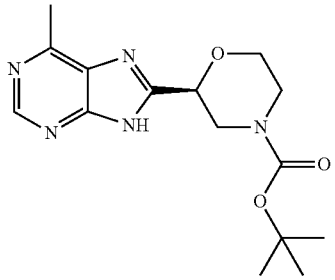 [SMILES: Cc1ncnc2[nH]c([C@@H]3CN(C(=O)OC(C)(C)C)CCO3)nc12]

A mixture of example 1b (4.14 g; 12.27 mmol) and lithium bromide (2.13 g; 24.5 mmol) in 1-propanol (80 ml) was heated at 90° C. over 14 days. The reaction mixture was absorbed on silica gel and purified by flash chromatography; eluent: EtOAc/MeOH/NH$_4$OH (from 9/1/0.1 to 8/2/0.2; volume/volume/volume). Obtained 3 g of the desired compound.

| HPLC-MS; Method: Z011_S03; R$_t$ [min]: 0.59 | MS: 320 (M + H)$^+$ |
|---|---|
| Chiral SFC; Method: I_IG_35_MEOH_NH$_3$_001 | R$_t$ [min]: 3.05; ee: 97.4% |

Example 2c

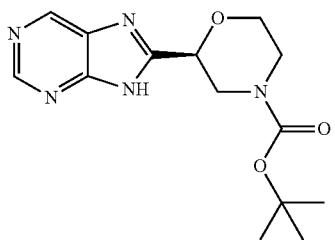 [SMILES: CC(C)(C)OC(=O)N1CCO[C@H](c2nc3cncnc3[nH]2)C1]

A mixture of example 1c (5.00 g, 15.5 mmol), potassium carbonate (2.14 g, 15.5 mmol) and isopropanol (50 ml) was stirred for 35 h at 80° C. The precipitate was filtered off, washed with isopropanol and the filtrate was concentrated in vacuo. The residue was dried overnight. Obtained 5.00 g of the desired product.

| Chiral SFC; Method: I_C4_20_MEOH_NH3_001; R$_t$ [min]: 2.64 min | MS: 306 (M + H)$^+$ ee: 85.4% |
|---|---|

Example 3b

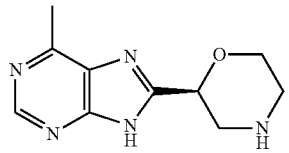 [SMILES: Cc1ncnc2[nH]c([C@@H]3CNCCO3)nc12]

Example 2b (3.50 g, 11.0 mmol) was dissolved in DCM (120 ml), HCl in dioxane (4 M, 13.7 ml, 55.0 mmol) was added dropwise under ice cooling. The reaction mixture was stirred for 2 h at rt. The reaction mixture was concentrated in vacuo at 35° C. Obtained 3.20 g of the desired compound as a salt which was used as such in the next step.

| Chiral SFC; Method: I_SA_25_MEOH_NH3_001; R$_t$ [min]: 2.42 min | MS: 220 (M + H)$^+$ e.e. 100% |
|---|---|

Example 3c

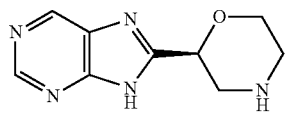 [SMILES: c1ncc2nc([C@@H]3CNCCO3)[nH]c2n1]

To a mixture of example 2c (9.40 g, 30.8 mmol) in DCM (1200 ml), HCl in dioxane (4 M, 35.0 ml, 140 mmol) was added dropwise and the reaction mixture was stirred overnight at rt. The solvents were evaporated in vacuo and the residue was re-evaporated 2× with toluene. Obtained 8.60 g of the desired product as a salt.

| Chiral SFC; Method: I_SA_20_MEOH_NH3_001; R$_t$ [min]: 4.27 min | MS: 206 (M + H)$^+$ ee: 100% |
|---|---|

Example 5a

Method C (According to Scheme 3)

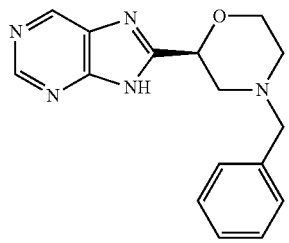 [SMILES: c1ccc(CN2CCO[C@H](c3nc4cncnc4[nH]3)C2)cc1]

A mixture of Example 1f (8.80 g, 28.1 mmol), LiBr (3.50 g, 40.3 mmol), MeOH (100 ml) and NMP (5 ml) was stirred 1.5 days at 120° C.

The crude was separated via column chromatography (DCM/MeOH/NH₃ 9/1/0.1; volume/volume/volume) followed by preparative HPLC and finally chiral SFC. Obtained 650 mg of the desired product.

| Chiral SFC; Method: I_C4_25_MEOH_NH3_001; R$_t$ [min]: 3.71 min | ee: 100% |
|---|---|

Example 6a

Method C (According to Scheme 3)

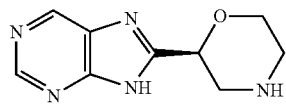 [SMILES: c1ncc2nc([C@@H]3CNCCO3)[nH]c2n1]

Example 5a (650 mg, 2.20 mmol) was dissolved in MeOH (30 ml) and Pd(OH)₂ (150 mg) was added and the reaction mixture was stirred 3 days at 50° C. and 3 bar H₂ pressure. The reaction mixture was filtered and the filtrate was concentrated in vacuo. Obtained 432 mg of the desired product.

| Chiral SFC; Method: I_IC_25_MEOH_NH3_001; R$_t$ [min]: 3.77 min; ee >95% | MS: 206 (M + H)⁺ |
|---|---|

Exemplary Embodiments

Example 2

(2,4-Difluorophenyl)methanol (229 μl; 2.05 mmol, CAS No. 56456-47-4), TEA (0.43 ml, 3.08 mmol) and Bis-[1,2,4]triazol-1-yl-methanone (337 mg; 2.05 mmol) were mixed together in DMF (6 ml); the reaction mixture was heated at 50° C. for 1 h. Example 3b (300 mg; 1.03 mmol) was then added and the reaction mixture was stirred at 50° C. overnight. After cooling down the reaction mixture was diluted with MeOH before being filtered and separated via semi-preparative HPLC. Obtained 52.5 mg of the desired compound.

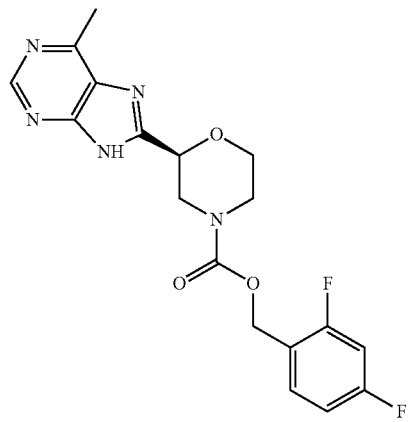 [SMILES: Cc1ncnc2[nH]c([C@@H]3CN(C(=O)OCc4ccc(F)cc4F)CCO3)nc12]

Example 2

| HPLC-MS; Method: Z011_S03; R$_t$ [min]: 0.64 | MS: 390 (M + H)⁺ |
| Chiral SFC; Method: I_IG_35_MEOH_NH₃_001 | Rt [min]: 3.22 ee: 72.8% |

Example 6

(2-Fluoro-4-methylphenyl)methanol (864 mg, 6.16 mmol, CAS No. 252004-38-9) and Bis-[1,2,4]triazol-1-yl-methanone (1.01 g; 6.16 mmol) were mixed together in DMF (18 ml); the reaction mixture was heated at 50° C. for 1 h. Example 3b (900 mg; 3.08 mmol) and TEA (1.29 ml, 9.24 mmol) were then added and the reaction mixture was stirred at 50° C. overnight. After cooling down the reaction mixture was concentrated in vacuo. The residue was diluted with H₂O and extracted with EtOAc. The organic layer was dried over Na₂SO₄, filtered and concentrated in vacuo. The crude was dissolved in THF before being filtered and separated via semipreparative HPLC. Obtained 180 mg of the desired compound which contained 16.5% of the R Enantiomer; consequently, the mixture was submitted to chiral SFC purification affording 130 mg of the desired S Enantiomer.

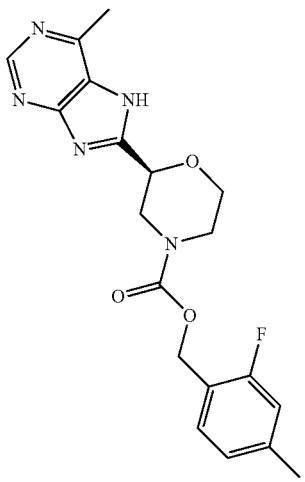 [SMILES: Cc1ccc(COC(=O)N2CCO[C@H](c3nc4ncnc(C)c4[nH]3)C2)c(F)c1]

Example 6

| HPLC-MS; Method: Z011_S03; R$_t$ [min]: 0.67 | MS: 386 (M + H)⁺ |
| Chiral SFC; Method: I_IG_35_MEOH_NH₃_001 | Rt [min]: 3.89; ee: 100% |

Example 7

Example 7 was synthesised in analogy to Example 6. Starting materials: Example 3b (300 mg, 1.03 mmol) and (2-Fluorophenyl)methanol (221 μl, 2.05 mmol, CAS No. 446-51-5). The reaction mixture was purified via preparative HPLC. Obtained 55.0 mg of the desired compound.

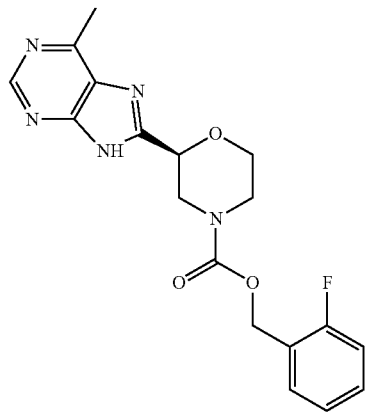 [SMILES: Cc1ncnc2[nH]c([C@@H]3CN(C(=O)OCc4ccccc4F)CCO3)nc12]

Example 7

| | |
|---|---|
| HPLC-MS; Method: Z011_S03; R$_t$ [min]: 0.63 | MS: 372 (M + H)$^+$ |
| Chiral SFC; Method: I_IG_35_MEOH_NH$_3$_001 | Rt [min]: 3.80; ee: 72.4% |

Example 8

(2-Fluoro-3-methylphenyl)methanol (189 mg; 1.35 mmol, CAS No. 307975-03-7), TEA (0.38 ml, 2.70 mmol) and Bis-[1,2,4]triazol-1-yl-methanone (295 mg; 1.80 mmol) were mixed together in DMF (6 ml); the reaction mixture was heated at 50° C. for 1 h. Example 3c (250 mg; 0.90 mmol) was then added and the reaction mixture was stirred for 2 h at 50° C. The reaction mixture was diluted with 4 ml of a mixture MeOH/Water before being filtered and separated via semipreparative HPLC. Obtained 178 mg of the desired compound.

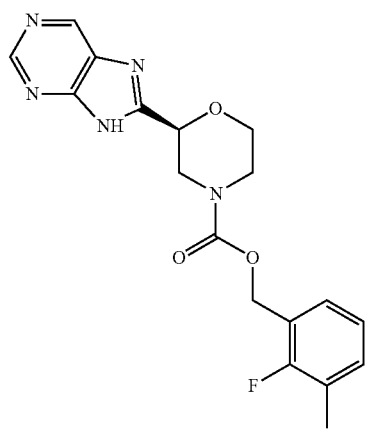 [SMILES: Cc1cccc(COC(=O)N2CCO[C@H](c3nc4cncnc4[nH]3)C2)c1F]

Example 8

| | |
|---|---|
| HPLC-MS; Method: Z011_S03; R$_t$ [min]: 0.69 | MS: 372 (M + H)$^+$ |
| Chiral SFC; Method: I_SA_20_MEOH_NH$_3$_001 | Rt [min]: 2.95 ee: 100% |

Example 9

Example 9 was synthesised in analogy to Example 2. Starting materials: Example 3c (250 mg, 0.90 mmol) and (3-Fluoro-2-methylphenyl)methanol (252 mg, 1.80 mmol, CAS No. 500912-13-0). The reaction mixture was purified via preparative HPLC. Obtained 113 mg of the desired compound.

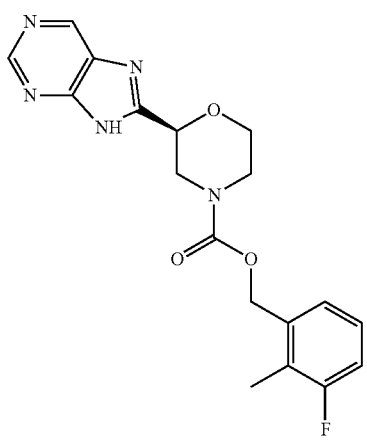 [SMILES: Cc1c(F)cccc1COC(=O)N1CCO[C@H](c2nc3cncnc3[nH]2)C1]

Example 9

| | |
|---|---|
| HPLC-MS; Method: Z011_S03; R$_t$ [min]: 0.67 | MS: 372 (M + H)$^+$ |
| Chiral SFC; Method: I_SA_20_MEOH_NH$_3$_001 | Rt [min]: 3.42 ee: 82.7% |

Example 10

Example 10 was synthesised in analogy to Example 6. Starting materials: Example 3c (350 mg; 1.44 mmol) and (4-Methylphenyl)methanol 353.8 mg (2.88 mmol). Obtained 230 mg of a product containing approximately 20% of the R enantiomer; the mixture was therefore separated via chiral SFC affording 143 mg of the desired S enantiomer.

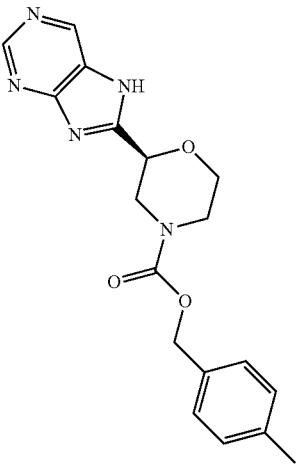 [SMILES: Cc1ccc(COC(=O)N2CCO[C@H](c3nc4ncncc4[nH]3)C2)cc1]

Example 10

| | |
|---|---|
| HPLC-MS; Method: Z011_S03; R$_t$ [min]: 0.67 | MS: 354 (M + H)$^+$ |
| Chiral SFC; Method: I_SA_20_MEOH_NH$_3$_001 | Rt [min]: 5.09 ee: 100% |

Example 11

Example 11 was synthesised in analogy to Example 2. Starting materials: Example 3b (250 mg, 0.86 mmol) and (4-Fluorophenyl)methanol (187 µl, 1.71 mmol, CAS No. 459-56-3). The reaction mixture was purified via preparative HPLC. Obtained 43 mg of the desired compound.

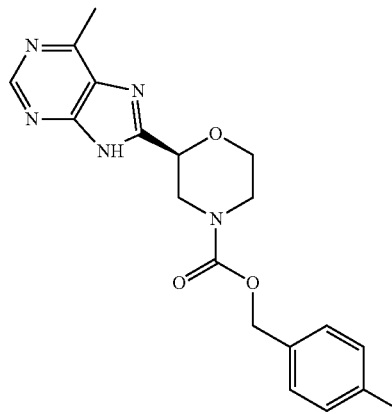

Example 11

| | |
|---|---|
| HPLC-MS; Method: Z011_S03; $R_t$ [min]: 0.64 | MS: 372 (M + H)$^+$ |
| Chiral SFC; Method: I_IG_35_MEOH_NH$_3$_001 | Rt [min]: 4.31 |
| | ee: 68.4% |

Example 13

(4-Fluorophenyl)methanol (194 µl; 1.80 mmol, CAS No. 459-56-3), DIPEA (548 µl, 3.15 mmol) and Bis-[1,2,4]triazol-1-yl-methanone (295 mg; 1.80 mmol) were mixed together in DMF (5 ml); the reaction mixture was heated at 50° C. for 1 h. Example 3c (250 mg; 0.90 mmol) was then added and the reaction mixture was stirred at 50° C. overnight. After cooling down the reaction mixture was diluted with H$_2$O and extracted with EtOAc. The organic layer was dried over Na$_2$SO$_4$, filtered and the solvent is removed in vacuo. The residue was triturated with DIPE, the obtained precipitate was filtered, dissolved in MeOH/DMF and separated via semipreparative HPLC. Obtained 105 mg of the desired compound.

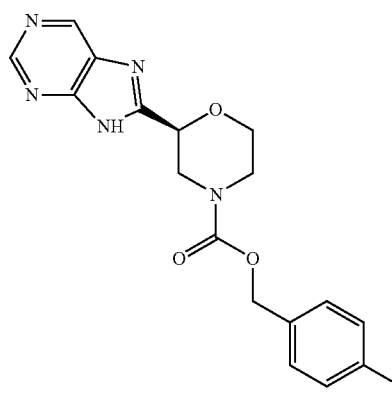

Example 13

| | |
|---|---|
| HPLC-MS; Method: Z011_S03; $R_t$ [min]: 0.62 | MS: 358 (M + H)$^+$ |
| Chiral SFC; Method: I_SA_20_MEOH_NH$_3$_001 | Rt [min]: 4.26 |
| | ee: 83.4 % |

Example 14

Example 14 was synthesised in analogy to Example 2. Starting materials: Example 3c (250 mg, 0.90 mmol) and (2,4-Difluorophenyl)methanol (0.20 ml, 1.80 mmol, CAS No. 56456-47-4). The reaction mixture was purified via preparative HPLC. Obtained 154 mg of the desired compound.

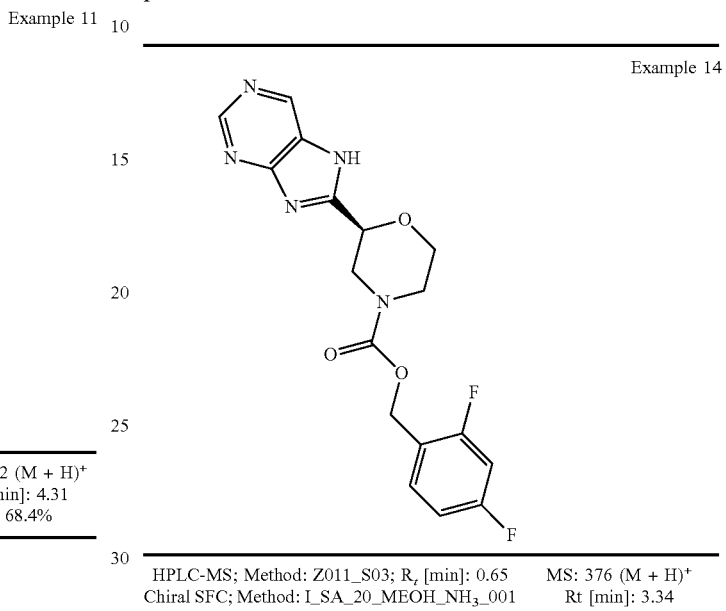

Example 14

| | |
|---|---|
| HPLC-MS; Method: Z011_S03; $R_t$ [min]: 0.65 | MS: 376 (M + H)$^+$ |
| Chiral SFC; Method: I_SA_20_MEOH_NH$_3$_001 | Rt [min]: 3.34 |
| | ee: 81.9% |

Example 16

Example 16 was synthesised in analogy to Example 2. Starting materials: Example 3c (200 mg, 0.72 mmol) and (3-Fluorophenyl)methanol (156 µl, 1.44 mmol, CAS No. 456-47-3). The reaction mixture was purified via preparative HPLC. Obtained 131 mg of the desired compound.

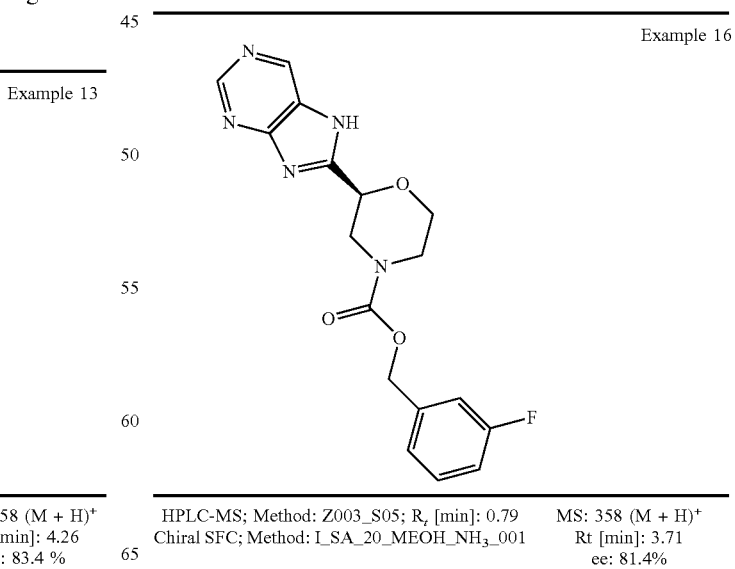

Example 16

| | |
|---|---|
| HPLC-MS; Method: Z003_S05; $R_t$ [min]: 0.79 | MS: 358 (M + H)$^+$ |
| Chiral SFC; Method: I_SA_20_MEOH_NH$_3$_001 | Rt [min]: 3.71 |
| | ee: 81.4% |

Example 17

(2-Fluorophenyl)methanol (155 µl; 1.44 mmol, CAS No. 446-51-5), DIPEA (438 µl, 2.52 mmol) and Bis-[1,2,4]triazol-1-yl-methanone (236 mg; 1.44 mmol) were mixed together in DMF (5 ml); the reaction mixture was heated at 50° C. for 1.5 h. Example 3c (200 mg; 0.72 mmol) was then added and the reaction mixture was stirred at 50° C. overnight. After cooling down the reaction mixture was diluted with H₂O and extracted with EtOAc. The organic layer was dried over Na₂SO₄, filtered and the solvent was removed in vacuo. The residue was dissolved in MeOH, filtered and separated via semipreparative HPLC. Obtained 98.3 mg of the desired compound.

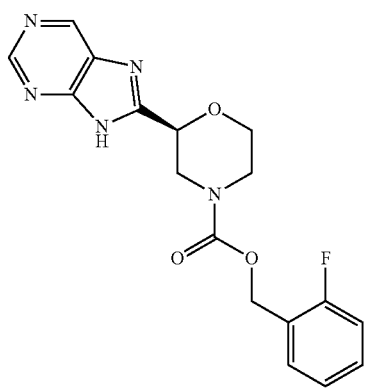 [SMILES: O=C(OCc1ccccc1F)N1CCO[C@H](c2nc3cncnc3[nH]2)C1]

Example 17

| HPLC-MS; Method: Z011_S03; $R_t$ [min]: 0.66 | MS: 358 (M + H)⁺ |
| Chiral SFC; Method: I_SA_20_MEOH_NH₃_001 | Rt [min]: 3.32 |
| | ee: 83.1% |

Example 18

(2,3-Difluorophenyl)methanol (162 µl; 1.44 mmol, CAS No. 75853-18-8), DIPEA (438 µl, 2.52 mmol) and Bis-[1,2,4]triazol-1-yl-methanone (236 mg; 1.44 mmol) were mixed together in DMF (5 ml); the reaction mixture was heated at 50° C. for 1.5 h. Example 3c (200 mg; 0.72 mmol) was then added and the reaction mixture was stirred at 50° C. overnight. The organic solvent was removed in vacuo. The residue was diluted with H₂O and the obtained precipitate was filtered off. The precipitate was triturated 2× with DIPE, filtered off and dried. Obtained 138 mg of the desired compound.

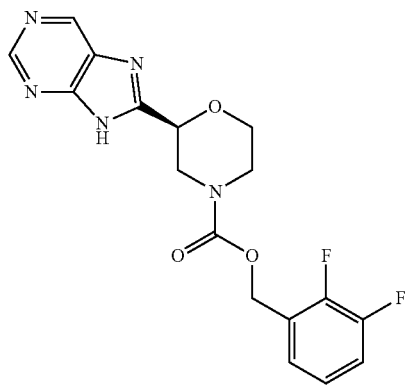 [SMILES: O=C(OCc1cccc(F)c1F)N1CCO[C@H](c2nc3cncnc3[nH]2)C1]

Example 18

| HPLC-MS; Method: Z011_S03; $R_t$ [min]: 0.67 | MS: 376 (M + H)⁺ |
| Chiral SFC; Method: I_SA_20_MEOH_NH₃_001 | Rt [min]: 3.23 |
| | ee: 100% |

Example 19

(2,6-Difluorophenyl)methanol (159 µl; 1.44 mmol, CAS No. 19064-18-7), DIPEA (438 µl, 2.52 mmol) and Bis-[1,2,4]triazol-1-yl-methanone (236 mg; 1.44 mmol) were mixed together in DMF (5 ml); the reaction mixture was heated at 50° C. for 1.5 h. Example 3c (200 mg; 0.72 mmol) was then added and the reaction mixture was stirred at 50° C. overnight. The residue was diluted with H₂O and stirred overnight at rt. The solvents were removed in vacuo. The residue was diluted with H₂O, the obtained precipitate was filtered off and dried. Obtained 68.9 mg of the desired compound.

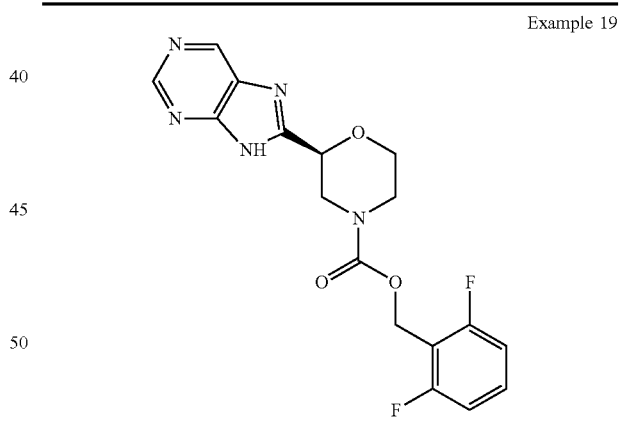

Example 19

| HPLC-MS; Method: Z011_S03; $R_t$ [min]: 0.63 | MS: 376 (M + H)⁺ |
| Chiral SFC; Method: I_SA_20_MEOH_NH₃_001 | Rt [min]: 2.80 |
| | ee: 89.8% |

Example 20

(4-Fluoro-2-methylphenyl)methanol (202 mg; 1.44 mmol, CAS No. 80141-91-9), DIPEA (0.38 ml, 2.16 mmol) and Bis-[1,2,4]triazol-1-yl-methanone (236 mg; 1.44 mmol) were mixed together in DMF (6 ml); the reaction mixture was heated at 50° C. for 1 h. Example 3c (200 mg; 0.72 mmol) was then added and the reaction mixture was stirred at 50° C. overnight. After cooling down the reaction mixture was diluted with H₂O/MeOH before being filtered and separated via semipreparative HPLC. Obtained 86.0 mg of the desired compound.

Example 20

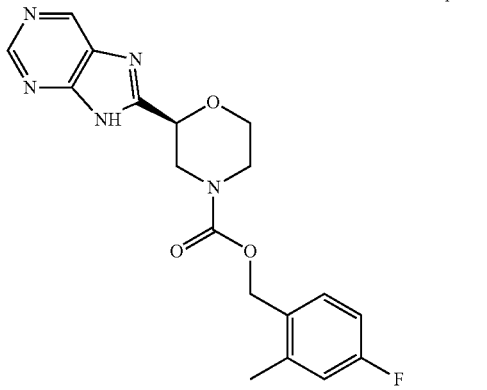

| HPLC-MS; Method: Z011_S03; R$_t$ [min]: 0.68 | MS: 372 (M + H)⁺ |
| Chiral SFC; Method: I_SA_20_MEOH_NH₃_001 | Rt [min]: 3.53 |
| | ee: 84.1% |

Example 21

Example 21 was synthesised in analogy to Example 8. Starting materials: Example 3b (250 mg, 0.86 mmol) and (4-Methylphenyl)methanol (209 mg, 1.71 mmol, CAS No. 589-18-4). The reaction mixture was purified via preparative HPLC. Obtained 50.0 mg of the desired compound.

Example 21

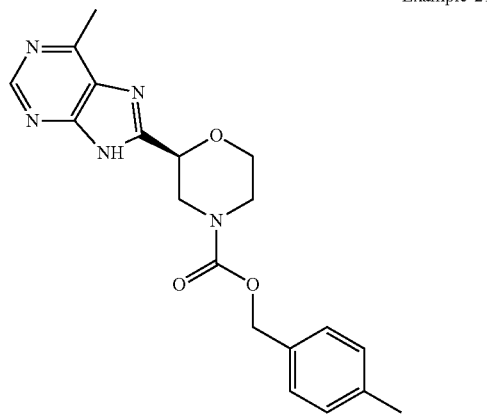

| HPLC-MS; Method: Z011_S03; R$_t$ [min]: 0.68 | MS: 368 (M + H)⁺ |
| Chiral SFC; Method: I_IG_35_MEOH_NH₃_001 | Rt [min]: 5.69 |
| | ee: 76.0% |

Example 24

[4-(Difluoromethyl)phenyl]methanol (24.0 mg; 0.15 mmol, CAS No. 444915-77-9) and CDI (23.0 mg; 0.14 mmol) were mixed together in DMF (0.5 ml); the reaction mixture was heated at 40° C. during 45 min. Example 3c (24.0 mg; 0.10 mmol), DIPEA (17.0 µl; 0.10 mmol) and DMF (0.5 ml) were then added in sequence and the reaction mixture was stirred overnight at 40° C. The reaction mixture was diluted with ACN/H₂O/MeOH, filtered and separated via semipreparative HPLC. Obtained 20.9 mg of the desired compound.

Example 24

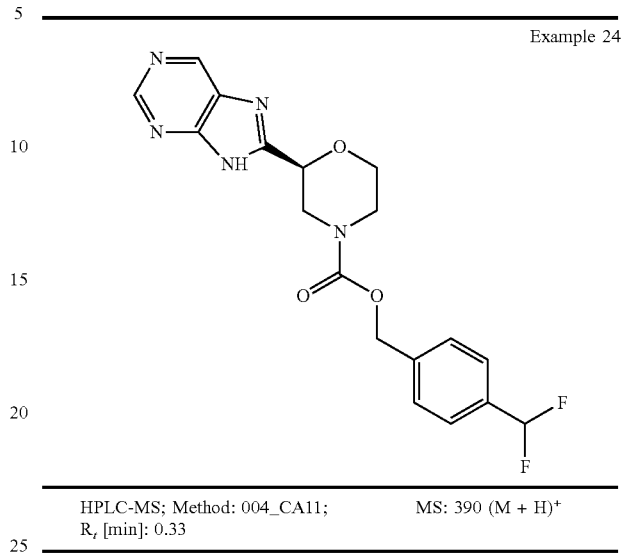

| HPLC-MS; Method: 004_CA11; | MS: 390 (M + H)⁺ |
| R$_t$ [min]: 0.33 | |

Example 25

Example 25 was synthesised in analogy to Example 24. Starting materials: Example 3c (24.0 mg, 0.10 mmol) and (4-Chlorophenyl)methanol (21.0 mg, 0.15 mmol, CAS No. 873-76-7). The reaction mixture was purified via preparative HPLC. Obtained 16.8 mg of the desired compound.

Example 25

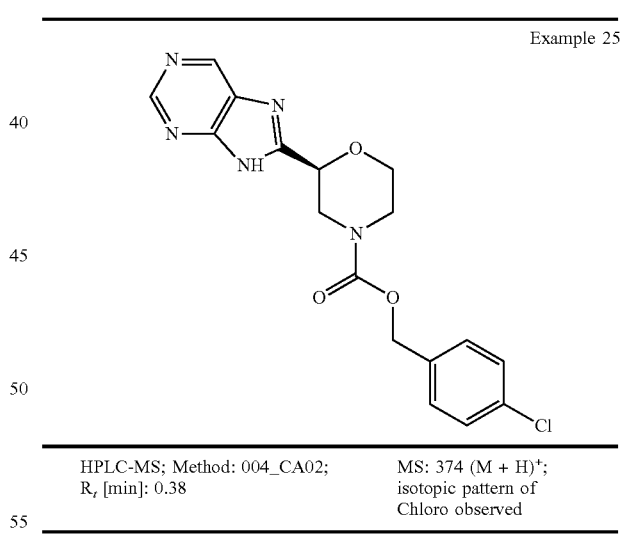

| HPLC-MS; Method: 004_CA02; | MS: 374 (M + H)⁺; |
| R$_t$ [min]: 0.38 | isotopic pattern of Chloro observed |

Example 26

Example 3c (25.0 mg; 0.10 mmol) and DIPEA (20.0 µl, 0.12 mmol) were dissolved in dioxane (1 ml), then Benzyl chloroformate (40.0 µl, 0.12 mmol, content 50%, CAS No. 501-53-1) was added dropwise under ice cooling and the reaction mixture was stirred overnight at rt.

The reaction mixture was concentrated in vacuo, dissolved in DMF and purified via preparative HPLC. Obtained 14.0 mg of the desired compound.

Example 26

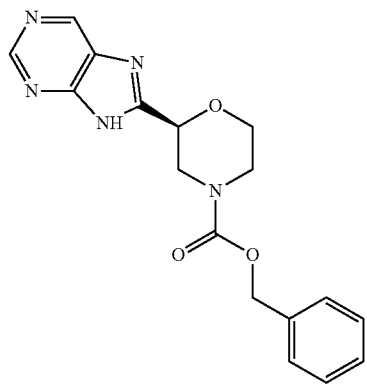 [SMILES: O=C(OCc1ccccc1)N1CCO[C@H](c2nc3cncnc3[nH]2)C1]

HPLC-MS; Method: Z018_S04; R$_t$ [min]: 0.81    MS: 340 (M + H)$^+$

Example 28

(2-Chlorophenyl)methanol (21.4 mg, 0.15 mmol, CAS No. 17849-38-6) and CDI (0.14 mmol) were mixed together in DMF (1 ml); the reaction mixture was stirred at rt during 1.5 h. Example 6a (20.5 mg, 0.10 mmol) dissolved in DMF (1 ml) was then added and the reaction mixture was stirred overnight at rt. The reaction mixture was separated via semipreparative HPLC. Obtained 7.1 mg of the desired compound.

Example 28

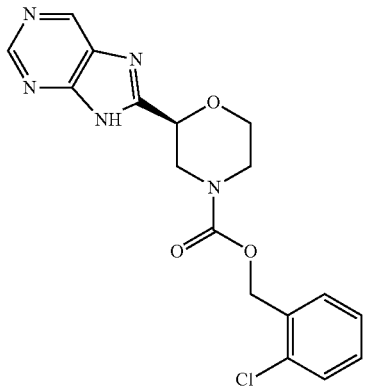 [SMILES: O=C(OCc1ccccc1Cl)N1CCO[C@H](c2nc3cncnc3[nH]2)C1]

HPLC-MS; Method: 003_CA11;    MS: 374 (M + H)$^+$;
R$_t$ [min]: 0.59    isotopic pattern of Chloro observed Example 29

Example 29 was synthesised in analogy to Example 28. Starting materials: Example 6a (20.5 mg, 0.10 mmol) and (3-Methylphenyl)methanol (18.3 mg, 0.15 mmol, CAS No. 587-03-1). The reaction mixture was purified via preparative HPLC. Obtained 3.4 mg of the desired compound.

Example 29

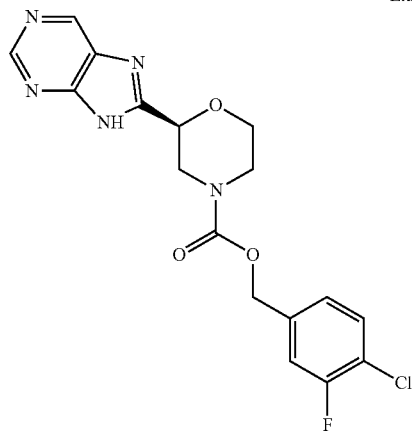

HPLC-MS; 003_CA11;    MS: 354 (M + H)$^+$
R$_t$ [min]: 0.59

Example 30

Example 30 was synthesised in analogy to Example 28. Starting materials: Example 6a (20.5 mg, 0.10 mmol) and (4-Chloro-3-fluorophenyl)methanol (24.1 mg, 0.15 mmol, CAS No. 202925-10-8). The reaction mixture was purified via preparative HPLC. Obtained 8.2 mg of the desired compound.

Example 30

HPLC-MS; Method: 003_CA11;    MS: 392 (M + H)$^+$;
R$_t$ [min]: 0.63    isotopic pattern of Chloro observed Example 31

Example 31 was synthesised in analogy to Example 28. Starting materials: Example 6a (20.5 mg, 0.10 mmol) and (3,4-Difluorophenyl)methanol (21.6 mg, 0.15 mmol, CAS No. 85118-05-4). The reaction mixture was purified via preparative HPLC. Obtained 5.4 mg of the desired compound.

Example 31

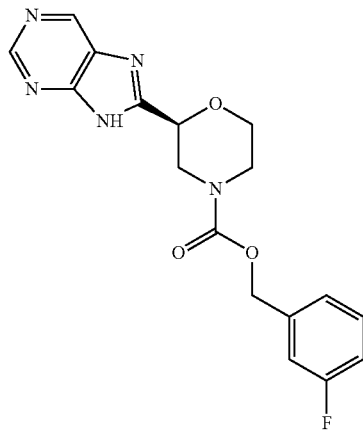

| HPLC-MS; Method: 003_CA11; | MS: 376 (M + H)+ |
| $R_t$ [min]: 0.58 | |

Example 32

Example 32 was synthesised in analogy to Example 28. Starting materials: Example 6a (20.5 mg, 0.10 mmol) and (2-Chloro-4-fluorophenyl)methanol (24.1 mg, 0.15 mmol, CAS No. 208186-84-9). The reaction mixture was purified via preparative HPLC. Obtained 8.1 mg of the desired compound.

Example 32

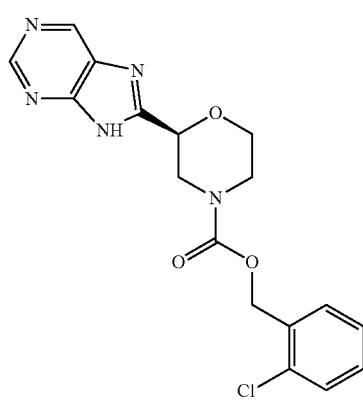

| HPLC-MS; Method: 003_CA11; | MS: 392 (M + H)+; |
| $R_t$ [min]: 0.62 | isotopic pattern of Chloro observed |

Example 34

Example 34 was synthesised in analogy to Example 28. Starting materials: Example 6a (20.5 mg, 0.10 mmol) and (3-Fluoro-4-methylphenyl)methanol (21.0 mg, 0.15 mmol, CAS No. 192702-79-7). The reaction mixture was purified via preparative HPLC. Obtained 6.2 mg of the desired compound.

Example 34

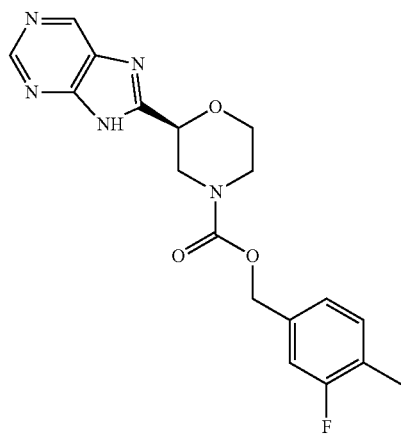 [SMILES: Cc1ccc(COC(=O)N2CCO[C@H](c3nc4cncnc4[nH]3)C2)cc1F]

| HPLC-MS; Method: 003_CA11; | MS: 372 (M + H)+ |
| $R_t$ [min]: 0.62 | |

Example 36

Example 36 was synthesised in analogy to Example 28. Starting materials: Example 6a (20.5 mg, 0.10 mmol) and (2-Fluoro-4-methylphenyl)methanol (21.0 mg, 0.15 mmol, CAS No. 252004-38-9). The reaction mixture was purified via preparative HPLC. Obtained 6.0 mg of the desired compound.

Example 36

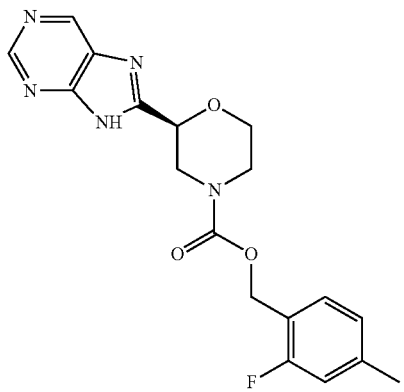 [SMILES: Cc1ccc(COC(=O)N2CCO[C@H](c3nc4cncnc4[nH]3)C2)c(F)c1]

| HPLC-MS; Method: 003_CA11; | MS: 372 (M + H)+ |
| $R_t$ [min]: 0.61 | |

Example 37

Example 37 was synthesised in analogy to Example 28. Starting materials: Example 6a (20.5 mg, 0.10 mmol) and (2-Fluoro-6-methylphenyl)methanol (21.0 mg, 0.15 mmol, CAS No. 478163-35-8). The reaction mixture was purified via preparative HPLC. Obtained 5.7 mg of the desired compound.

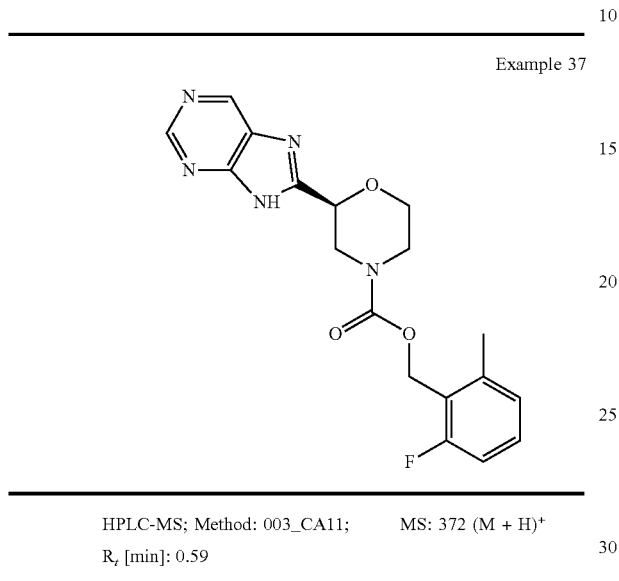

Example 37

HPLC-MS; Method: 003_CA11; MS: 372 (M + H)$^+$
R$_t$ [min]: 0.59

Example 38

Example 38 was synthesised in analogy to Example 28. Starting materials: Example 6a (20.5 mg, 0.10 mmol) and (2,4,6-Trifluorophenyl)methanol (24.3 mg, 0.15 mmol, CAS No. 118289-07-9). The reaction mixture was purified via preparative HPLC. Obtained 9.1 mg of the desired compound.

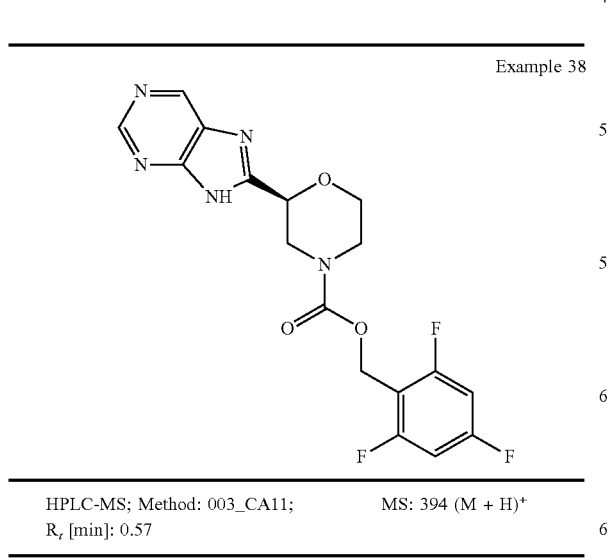

Example 38

HPLC-MS; Method: 003_CA11; MS: 394 (M + H)$^+$
R$_t$ [min]: 0.57

The invention claimed is:

1. A compound of formula A

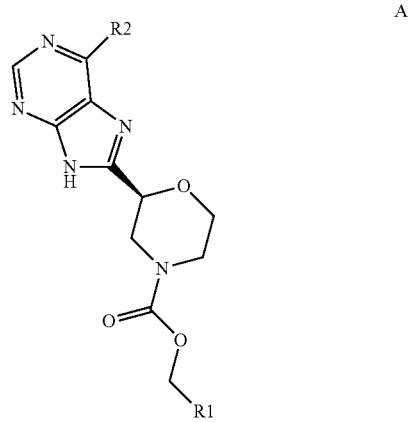

A in which

R$^1$ represents phenyl which is optionally substituted with 1, 2 or 3 substituents selected from the group consisting of fluoro, chloro, methyl, ethyl, cyclopropyl, F$_2$HC—, FH$_2$C—, and F$_3$C—;

R$^2$ represents hydrogen, or methyl, or a pharmaceutically acceptable salt thereof.

2. The compound according to claim 1, wherein R$^2$ represents hydrogen, or a pharmaceutically acceptable salt thereof.

3. The compound according to claim 1, wherein R$^2$ represents methyl, or a pharmaceutically acceptable salt thereof.

4. The compound according to claim 1 wherein R$^1$ represents phenyl which is optionally substituted with 1, 2 or 3 substituents selected from the group consisting of fluoro, chloro, methyl, and F$_2$HC—, or a pharmaceutically acceptable salt thereof.

5. The compound according to claim 1 wherein R$^1$ represents

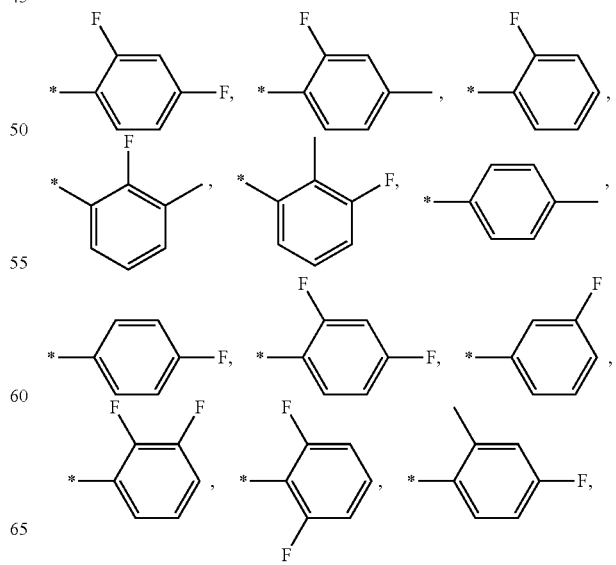

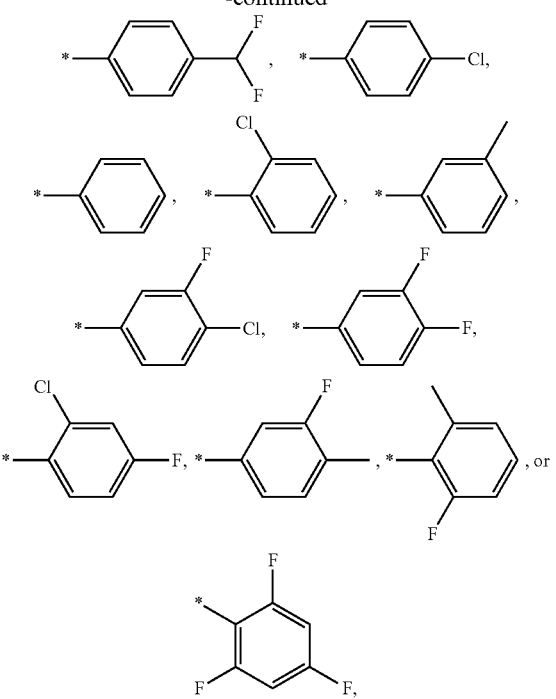
or a pharmaceutically acceptable salt thereof.
6. The (S)-enantiomer according to claim 1 selected from the group consisting of:
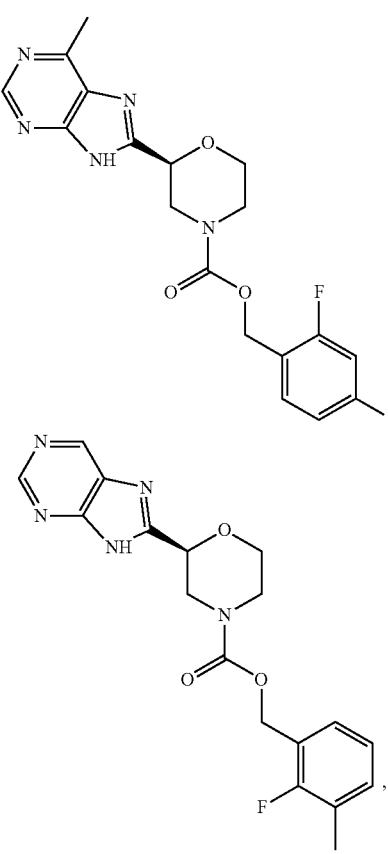
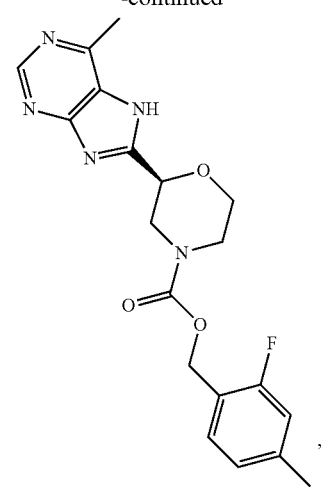
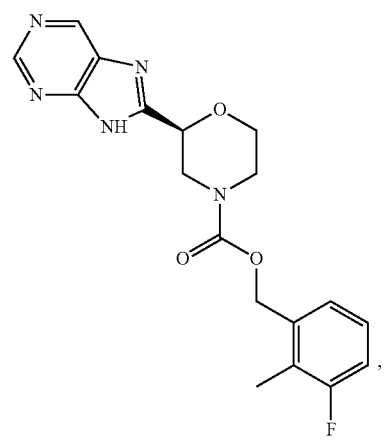

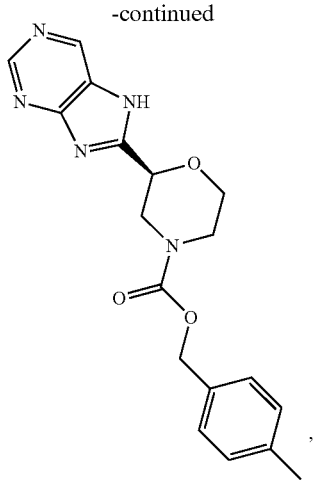
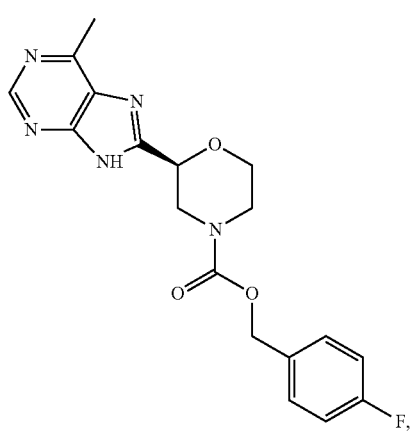
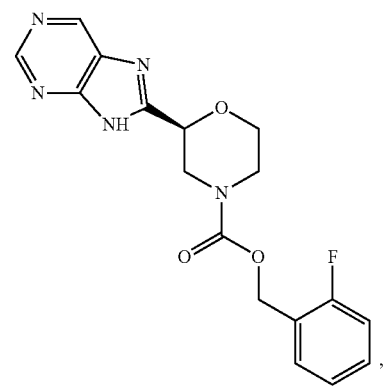
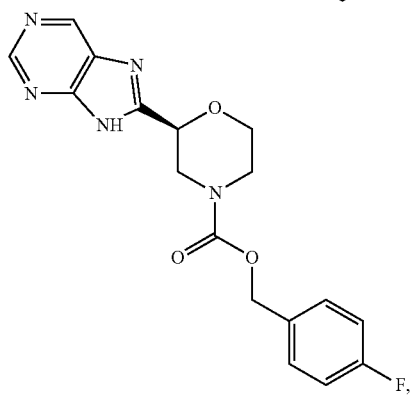
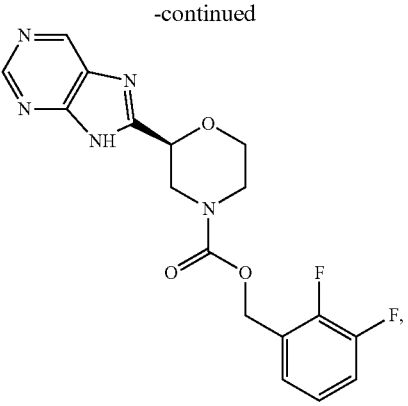
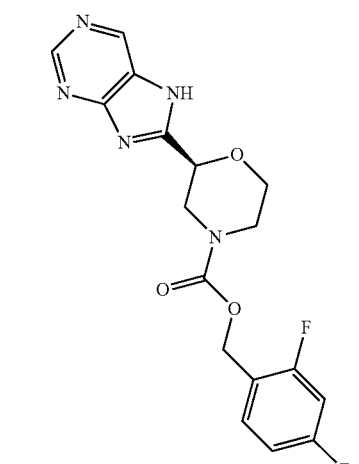
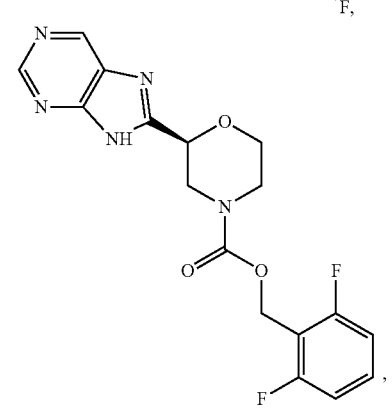
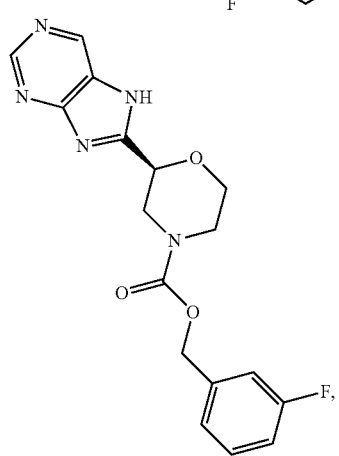

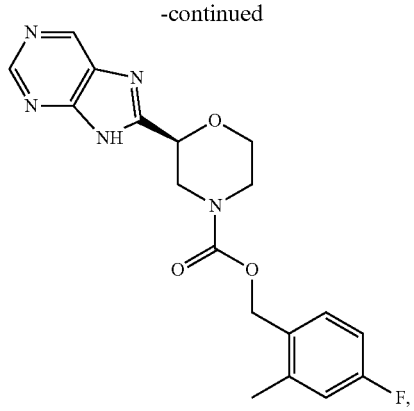
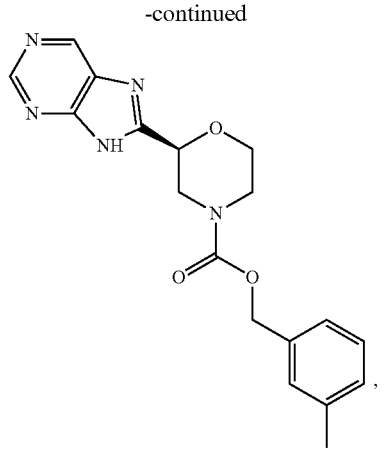

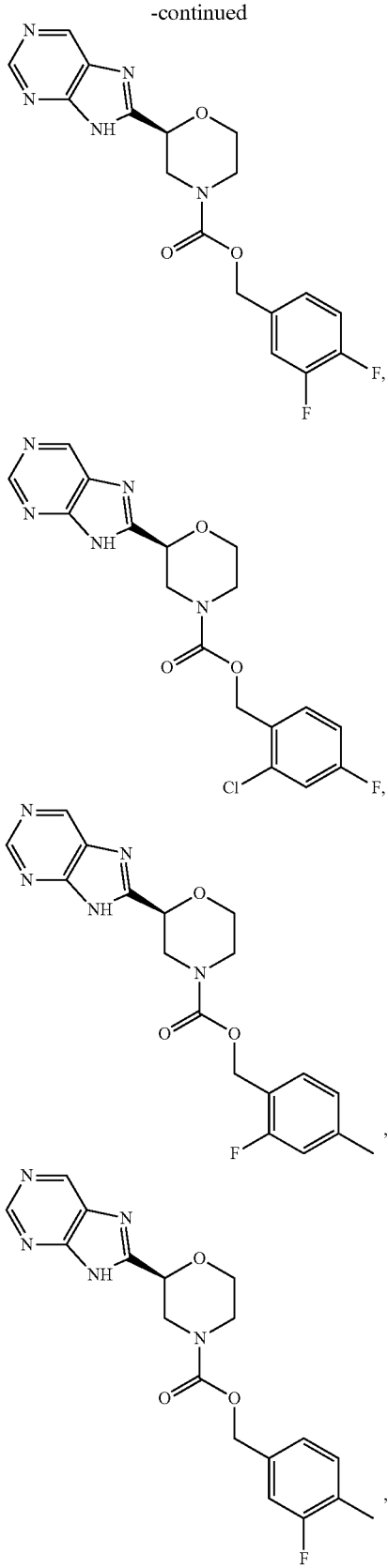

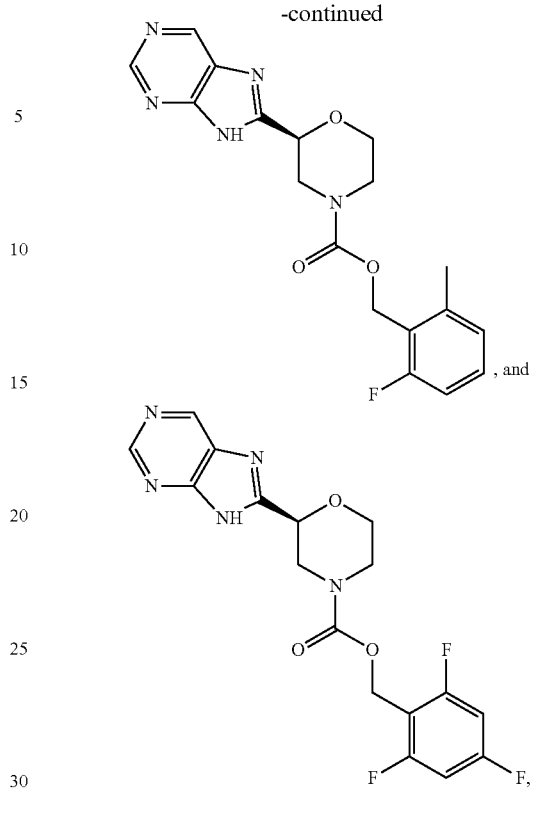

or a pharmaceutically salt thereof.

7. A pharmaceutically acceptable salt of a compound according to claim 1.

8. A method of treating depression, comprising a step of administering to a patient in need thereof a pharmaceutically effective amount of a compound according to claim 1, or a pharmaceutically acceptable salt thereof.

9. A method of treating bipolar disorder I depressed, hypomanic, manic and mixed form; bipolar disorder II; depressive disorders, such as single depressive episode or recurrent major depressive disorder, minor depressive disorder, depressive disorder with postpartum onset, depressive disorders with psychotic symptoms; major depressive disorder with or without concomitant anxious distress, mixed features, melancholic features, atypical features, mood-congruent psychotic features, mood-incongruent psychotic features, or catatonia, said method comprising the step of administering to a patient in need thereof a pharmaceutically effective amount of a compound according to claim 1 or a pharmaceutically acceptable salt thereof.

10. The method of treatment according to claim 9, wherein the compound, or a pharmaceutically acceptable salt thereof, is administered in addition to treatment with another antidepressant drug.

11. The method of treatment according to claim 9, wherein the compound, or a pharmaceutically acceptable salt thereof, is administered in addition to behavioural therapy.

12. The method of treatment according to claim 9, wherein the compound, or a pharmaceutically acceptable salt thereof, is in an admixture with a pharmaceutically acceptable adjuvant, diluent and/or carrier.

* * * * *